United States Patent [19]

Naka et al.

[11] Patent Number: 5,082,838
[45] Date of Patent: Jan. 21, 1992

[54] SULFUR-CONTAINING FUSED PYRIMIDINE DERIVATIVES, THEIR PRODUCTION AND USE

[75] Inventors: Takehiko Naka; Norio Shimamoto, both of Kobe; Taketoshi Saijo, Ikeda; Masahiro Suno, Kobe, all of Japan

[73] Assignee: Takeda Chemical Industries, Ltd., Osaka, Japan

[21] Appl. No.: 538,071

[22] Filed: Jun. 13, 1990

[30] Foreign Application Priority Data

Jun. 21, 1989 [JP] Japan .................. 1-156725

[51] Int. Cl.$^5$ ................ C07D 515/00; C07D 513/00; A61K 31/55; A61K 31/505
[52] U.S. Cl. ........................ 514/211; 514/224.2; 514/258; 540/552; 544/48; 544/278
[58] Field of Search .............. 544/278, 48; 514/258, 514/224.2, 211; 540/552

[56] References Cited

U.S. PATENT DOCUMENTS 4,394,505  7/1983  Kamata et al. ................. 544/91

OTHER PUBLICATIONS

Tetrahedron, vol. 28, pp. 4737–4746 (1972), Tsuge et al., "Studies of Acyl and Thioacyl Isocyanates X$^1$ The Reactions of Benzoyl and Thiobenzoyl Isocyanates with 2-Thiazolines and 2-Oxazolines".

J. C. S. Perkin I, (1972), pp. 2385–2391, Brown et al., "The Synthesis of Some 1-Substituted Cytosine and Uracil Derivatives".

Jnl. of Pharm. Sciences, vol. 71, No. 8, Aug. 1982, pp. 897–900, Kaul et al., "2-$^{14}$C-1-Allyl-3,5-Diethyl-6-Chlorouracil II: Isolation and Structures . . . ".

Arzneim-Forsch/Drug Res. 32(I), No. 6 (1982) Kaul et al., "Identifizierung eines Dritten S-Haltigen Metaboliten von 1-Allyl-3,5-Diethyl-6-Chloruracil und Bildungsmechanismus der SCH$_3$-Metaboliten".

Xenobiotica, vol. 12, No. 8, 1982, pp. 495–498, Kaul et al., "Structure of a Novel Sulphur-Containing Metabolite of Acluracil (1-Allyl-3,5-Diethyl-6-Chlorouracil)".

Primary Examiner—Mukund J. Shah
Assistant Examiner—Matthew V. Grumbling
Attorney, Agent, or Firm—Wegner, Cantor, Mueller & Player

[57] ABSTRACT

Disclosed is a compound represented by the formula (I) or a salt thereof:

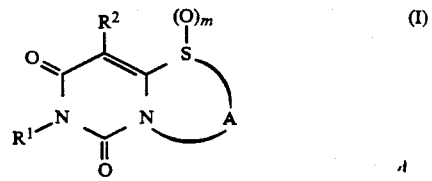

wherein $R^1$ represents an aliphatic hydrocarbon, aralkyl or aryl group which may be substituted; $R^2$ represents hydrogen, an aliphatic hydrocarbon group having one or more substituents, an aryl group which may be substituted, an amino group which may be substituted, a formyl group, a nitro group or a halogeno group; A represents a divalent hydrocarbon chain of 2 to 4 carbon atoms which may be substituted; and m represents an integer of 0 to 2, which is useful for treatment and prevention of diseases induced by abnormalities in regulation of reactions in vivo mediated through endothelin or interleukin 1, and of immune diseases and inflammatory diseases.

26 Claims, No Drawings

SULFUR-CONTAINING FUSED PYRIMIDINE DERIVATIVES, THEIR PRODUCTION AND USE

BACKGROUND OF THE INVENTION

The present invention relates to novel sulfur-containing fused pyrimidine derivatives useful as medicines.

Autacoids which are produced in vivo and exhibit various pharmacological actions in the small amounts thereof which are liberated from cells by stimulation of some kind, and act on cells and organs in the vicinity of production sites thereof to play an important role in the expression, the maintenance and the regulation of various physiological functions.

Vascular endothelial cells produce various biologically active substances, thereby regulating vasoactivity and hemocyte functions. In particular, prostacyclin ($PGI_2$) and endothelium-derived relaxation factors (EDRF) have been noted as factors for relaxing vascular smooth muscles. It has recently been found that one of the endothelium-derived relaxation factors is nitrogen monoxide (NO) or an analogue thereof.

On the other hand, it was also reported that the endothelial cells produced the factors for constricting vascular smooth muscles (ECOF) under various stimulation conditions such as anoxia. In 1988, M. Yanagisawa et al. succeeded in isolating a vasoconstrictor substance from the culture supernatant of the endothelial cells of porcine aortae [M. Yanagisawa et 1., *Nature* 332, 411 (1988)]. This substance, consisting of 21 amino acid residues and 2 intramolecular disulfide bonds, was named "endothelin (ET)". The endothelin strongly contracts various smooth muscles (such as tracheal smooth muscles) including vascular smooth muscles (such as coronary arteries, aortae and basilar arteries) of animals including human. The activities are strong more than 10 times as strong as those of known constrictor peptides such as angiotensin II, vasopressin and neuropeptide Y, and it is not affected by receptor antagonists or synthetic inhibitors of known vasoactive substances such as serotonin, norepinephrine, thromboxane $A_2$ and leukotriene. It is known that only calcium antagonists partially inhibit their activities. It has recently become clear that the endothelin has not only smooth muscle constrictor activity, but also various physiological activities. For example, the endothelin promotes secretion of atrial natriuretic peptides in cultured rat atrial muscles, and inhibits renin secretion from juxtaglomerular cells. However, it is not entirely revealed till now what physiological role endothelin plays in vivo and what pathology endothelin is concerned with. Considering the various activities of the endothelin and the distribution of endothelin receptors over a wide range from vascular vessel systems to brains, the endothelin might relate to various diseases such as renal, pulmonary and cardiac diseases. It is further anticipated that the endothelin acts as a hormone or an autacoid controling circulation or as a neurotransmitter.

Nerve growth factor (NGF) is a polypeptide having 118 amino acids. NGF is a neurotrophic factor necessary for differentiation and survival in peripheral, sensory and central neurons In the brain, NGF is distributed in cerebral cortex and hippocampus, and acts as a neurotrophic factor for cholinergic neurons in basal forebrain. In the case of patients suffering from Alzheimer's disease, degeneration of cholinergic neurons in basal forebrain is significantly involved, and it is believed that impairment of learning and memory of the disease is due to this degeneration [M. Goedert et al., *Mol. Brain Res.*, 1, 85–92 (1986)]. Recently, it has been reported that in various animal models with cerebral lesion NGF prevents the degeneration of cholingergic neurons and improves the impairment of learning and memory [F. Hefti, *J. Neuroscience*, 6, 2155–2162 (1986); V. Pallage, *Brain Res.*, 386, 197–208 (1986)]. From these findings, NGF draws an attention as the most effective candidate for the treatment of Alzheimer's disease.

On the other hand, interleukin-1 (IL-1) known as an inflammatory autacoid is produced and secreted mainly in stimulated monocytes or macrophages. Recently, it has been shown that Il-1 can be produced by many types of cells including endothelial cells or fibroblasts.

Furthermore, IL-1 acts on various types of cells and is involved in many functions. First, relating to immune or inflammatory reactions, it makes lymphocytes, T and B cells, to differentiate or to proliferate increasing their production of cytokines such as IL-2 of CSFs. It acts on endothelial cells and play important roles in fibrinogenesis or lymphocyte adhesion, and acts on hepatocytes to make acute phase proteins. Second, it relates to connective tissue cells. It causes fibroblast or synovial cells to proliferate. However, it induces protease production and reduce the extracellular matrix proteins on these cells causing tissue damages. Similarly, it acts on chondrocytes or bone cells. Third, the action of IL-1 on nervous cells is also becoming clear.

SUMMARY OF THE INVENTION

It is therefore a primary object of the present invention to provide compounds useful for treatment and prevention of various diseases induced by abnormalities in regulation of various reactions in vivo mediated through endothelin or interleukin-1 of various autacoids produced in vivo, for example, diseases such as myocardial infarction, angina pectoris and renal failure, and various immune diseases and inflammatory diseases, as well as rheumatism, by inhibiting the above-mentioned reactions in vivo.

Further object of the present invention is to provide compounds useful for treatment of cerebral lesions and memory impairment (for example, in Alzheimer's disease) through inducing the production of NGF.

Other objects of the present invention will become apparent from the following description.

The present inventors conducted intensive investigations to provide compounds useful for treatment and prevention of diseases such as myocardial infarction, angina pectoris and renal failure, various immune diseases and inflammatory diseases, and cerebral lesions and memory impairment (for example in Alzheimer's disease), and consequently discovered that specific sulfur-containing condensed pyrimidine derivatives could attain these objects, thus arriving at the present invention.

In accordance with the present invention, there is provided a compound represented by the following formula (I) or a pharmaceutically acceptable salt thereof:

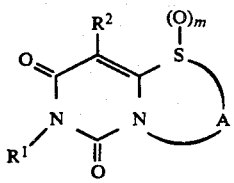

wherein R¹ represents an aliphatic hydrocarbon, aralkyl or aryl group which may be substituted; R² represents hydrogen, an aliphatic hydrocarbon group having one or more substituents, an aryl group which may be substituted, an amino group which may be substituted, a formyl group, a nitro group or a halogeno group; A represents a divalent hydrocarbon chain of 2 to 4 carbon atoms which may be substituted; and m represents an integer of 0 to 2.

DESCRIPTION OF THE PREFERRED EMBODIMENTS

Of the sulfur-containing condensed pyrimidine derivatives included in the present invention such as thiazolo[3,2-c]pyrimidine-5,7(6H)-diones[carbon number of chain A is 2], pyrimido[6,1-b][1,3]thiazine-6,8(7H)-diones [carbon number of chain A is 3] and pyrimido[6,1-b][1,3]thiazepin-7,9(8H)-diones[carbon number of chain A is 4], the pyrimido[6,1-b][1,3]thiazepin-7,9(8H)-diones are compounds which are novel in their skeleton itself and not described in the literature.

With respect to the thiazolo[3,2-c]pyrimidine-5,7(6H)-dione derivatives, for example, 6,8-diethyl-2-hydroxymethyl-2,3-dihydrothiazolo[3,2-c]pyrimidine-5,7(6H)-dione is reported as a metabolite of 1-allyl-3,5-diethyl-6-chlorouracil [R. Kaul et al., *J. Pham. Sci.* 71, 897 (1982); *Xenobiotica* 12, 495 (1982); *Arzneim-Forsch.* 32, 610 (1982)]. However, there is no report of its systematic synthesis. Also as to the pyrimido[6,1-b][1,3]thiazine-6,8(7H)-dione derivatives, for example, perhydropyrimido[6,1-b][1,3]thiazine-6,8-dione derivatives are reported in D. M. Brown et al., *J. Chem. Soc.*, 2385 (1972). However, there is no report of the systematic synthesis of these derivatives.

Also, no pharmacological actions of these derivatives are known at all.

With reference to the above-mentioned formula (I), examples of the aliphatic hydrocarbon groups represented by R¹ include alkyl groups of about 1 to 8 carbon atoms such as methyl, ethyl, propyl, i-propyl, butyl, i-butyl, sec-butyl, pentyl, i-pentyl, hexyl, heptyl and octyl; and alkenyl groups of about 2 to 8 carbon atoms such as vinyl, allyl, 1-propenyl, isopropenyl, 2-butenyl, 1,3-butadienyl, 2-pentenyl, 1-hexenyl, 1-heptenyl and 1-octenyl. The substituents of the aliphatic hydrocarbon groups represented by R¹ include, for example, cyano, carbamoyl, heteroaryl (such as pyridyl or quinolyl), hydroxyl, lower ($C_1$ to $C_4$) alkoxy, amino, lower ($C_1$ to $C_4$) alkyl, carboxyl, ester(such as lower ($C_1$ to $C_4$) alkoxy carbonyl) and amido (such as lower ($C_2$ to $C_6$) alkanoylamino) groups. The aralkyl groups include groups obtained by combining aryl groups such as phenyl and naphthyl with alkylene groups of about 1 to 4 carbon atoms such as methylene, ethylene, trimethylene and tetramethylene. The aryl group may be substituted by, for example, 1 to 3 halogen atoms (such as fluorine, chlorine or bromine), lower ($C_1$ to $C_4$) alkyl (such as methyl or ethyl), aryl which may be substituted (such as phenyl or o-cyanophenyl), alkoxy (such as methoxy or ethoxy) or nitro groups.

The aryl groups represented by R¹ include phenyl and naphthyl, and may be substituted by, for example, 1 to 3 halogen atoms (such as fluorine, chlorine or bromine), lower ($C_1$ to $C_4$) alkyl (such as methyl or ethyl), alkoxy (such as methoxy or ethoxy) or nitro groups.

The aliphatic hydrocarbon groups having substituents represented by R² include, for example, alkyl groups of about 1 to 8 carbon atoms and alkenyl groups of about 2 to 8 carbon atoms having substituents. The substituents include cyano, carbamoyl, aryl as defined herein above, hydroxyl, alkoxy, amino, alkyl, carboxyl, ester and amido groups. Specific examples thereof include groups represented by the formulae:

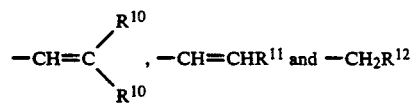

wherein $R^{10}$ represents a cyano, carbamoyl or lower ($C_1$ to $C_4$) alkoxycarbonyl group; $R^{11}$ represents a lower ($C_1$ to $C_8$) alkyl, aryl as defined herein above, cyano, carbamoyl or lower ($C_1$ to $C_4$) alkoxycarbonyl group; and $R^{12}$ represents a dialkyl-substituted amino group such as dimethylamino, diethylamino, morpholino, piperidino or piperazino.

The aryl groups represented by R² include phenyl and naphthyl, and may be substituted by, for example, 1 to 3 halogen atoms (such as fluorine, chlorine or bromine), lower ($C_1$ to $C_4$) alkyl (such as methyl or ethyl), alkoxy (such as methoxy or ethoxy) or nitro groups.

The unsubstituted or substituted amino group represented by R² is denoted by the formula:

wherein each of $R^8$ and $R^9$ is hydrogen, a lower alkyl group having about 1 to 8 carbon atoms (such as methyl, ethyl, propyl or butyl) or a fatty acid-derived acyl group having about 1 to 8 carbon atoms (such as formyl, acetyl, propionyl or butyryl).

The halogeno groups represented by R² include fluorine, chlorine, bromine and iodine.

The above-mentioned unsaturated or saturated divalent hydrocarbon chains of 2 to 4 carbon atoms represented by A include chains represented by the formula

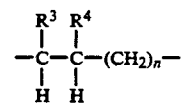

wherein R³ represents hydrogen, an lower ($C_1$ to $C_4$) alkyl group which may be substituted by halogen atom, lower ($C_1$ to $C_4$) alkylthio or phenylthio (such as chloromethyl, alkylthiomethyl or phenylthiomethyl), —YR⁵ [wherein Y is —O— or —S—, and R⁵ is hydrogen, a lower alkyl group of 1 to 4 carbon atoms (such as methyl or ethyl) or an aryl group (such as phenyl or naphthyl) which may be substituted (such as alkyl of 1 to 4 carbon atoms, alkoxy of 1 to 4 carbon atoms or phenyl which may be substituted by one to three halogen atoms)], or a fatty acid-derived lower acyl group of 1 to 4 carbon atoms (such as acetyl or trifluoroacetyl); $R^4$ represents hydrogen or a lower alkyl group of 1 to 4 carbon atoms (such as methyl or ethyl); and n represents an integer of 0 to 2.

The unsaturated or saturated divalent hydrocarbon chains of 2 to 4 carbon atoms represented by A also include chains represented by the formula:

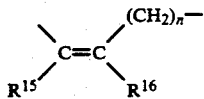

wherein $R^{15}$ and $R^{16}$ represent hydrogen atoms, lower alkyl groups of 1 to 4 carbon atoms (such as methyl or ethyl), —$COOR^{17}$ wherein $R^{17}$ is hydrogen atom or lower ($C_1$ to $C_4$) alkyl or —$NHR^{18}$ wherein $R^{18}$ is hydrogen atom, lower ($C_1$ to $C_4$) alkyl or lower alkanoyl; and n represents an integer of 0 to 2.

The unsaturated or saturated divalent hydrocarbon chains of 2 to 4 carbon atoms represented by A further include chains represented by the formula

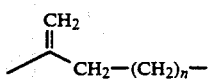

wherein n represents an integer of 0 to 2.

In this specification, the word "lower" before an alkyl moiety designates a preference for 1—4 carbon atoms.

Of the above-mentioned compounds represented by formula (I), the compounds in which $R^1$ is an alkyl group of 3 to 8 carbon atoms or an aralkyl group which may be substituted, $R^2$ is an aryl group which may be substituted, and A is a divalent hydrocarbon chain of 2 to 3 carbon atoms are particularly preferred.

The salts of the compounds represented by formula (I) include pharmacologically acceptable salts, for example, acid-addition salts, namely inorganic salts such as hydrochlorides, hydrobromides, sulfates, nitrates and phosphates, and organic salts such as acetates, tartrates, citrates, fumarates and maleates.

Manufacturing Method

The compounds represented by formula (I) can be produced by the following methods.

Reaction (a):

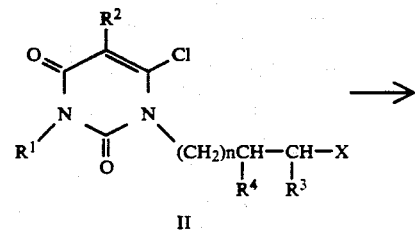

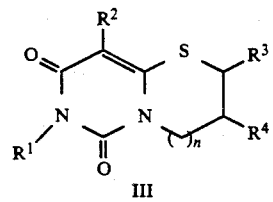

wherein $R^1$, $R^2$, $R^3$ and $R^4$ have the same meanings as given above, X represents a halogen atom, and n represents an integer of 0 to 2.

Reaction (b):

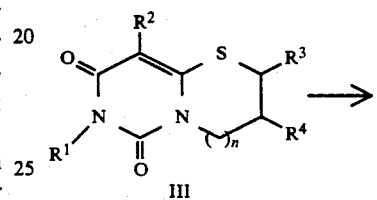

wherein $R^1$, $R^2$, $R^3$, $R^4$ and n have the same meanings as given above.

Reaction (c):

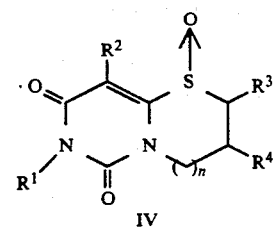

wherein $R^1$, $R^2$, $R^3$, $R^4$ and n have the same meanings as given above.

Reaction (d):

-continued

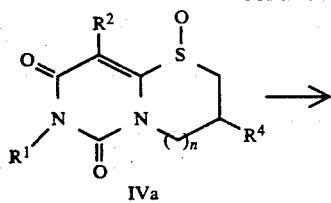
IVa

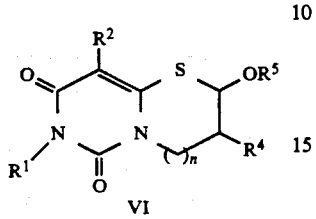
VI wherein $R^1$, $R^2$, $R^4$, $R^5$ and n have the same meanings as given above.

Reaction (e)

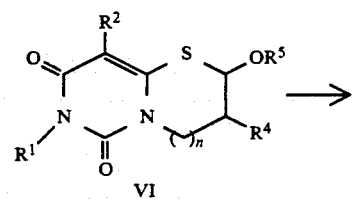
VI

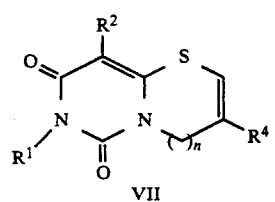
VII wherein $R^1$, $R^2$, $R^4$, $R^5$ and n have the same meanings as given above.

Reaction (f):

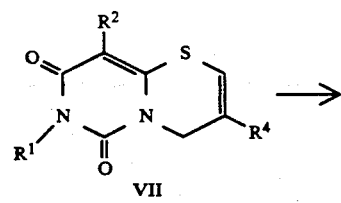
VII

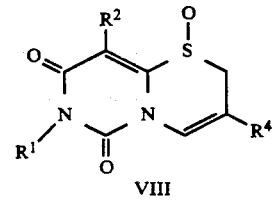
VIII wherein $R^1$, $R^2$ and $R^4$ have the same meanings as given above.

Reaction (g):

-continued

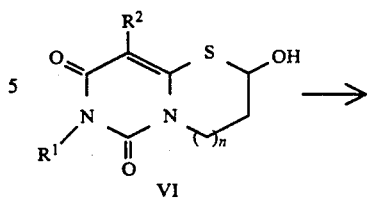
VI

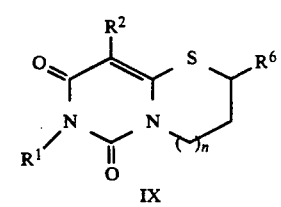
IX wherein $R^1$, $R^2$ and n have the same meanings as given above; and $R^6$ represents an alkylthio group having about 1 to 4 carbon atoms, an alkoxy group having about 1 to 4 carbon atoms, or an arylthio or aryloxy group which may be substituted.

Reaction (h):

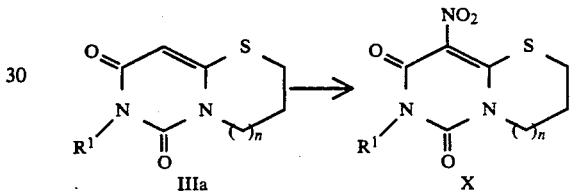
IIIa     X wherein $R^1$ and n have the same meanings as given above.

Reaction (i):

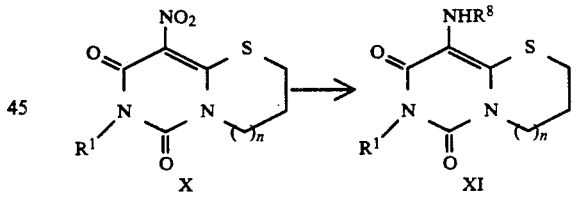
X     XI wherein $R^1$, $R^8$ and n have the same meanings as given above.

Reaction (j):

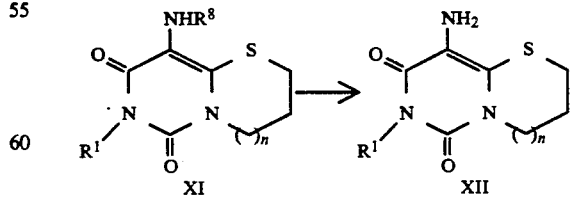
XI     XII wherein $R^1$, $R^8$ and n have the same meanings as given above.

Reaction (k):

-continued

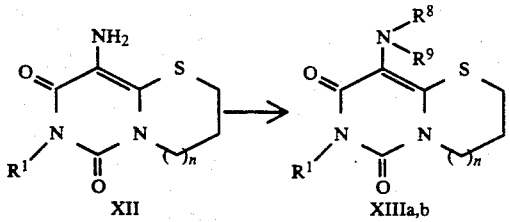

wherein $R^1$, $R^8$, $R^9$ and n have the same meanings as given above.

Reaction (l):

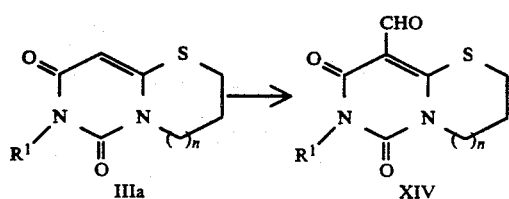

wherein $R^1$ and n have the same meanings as given above.

Reaction (m):

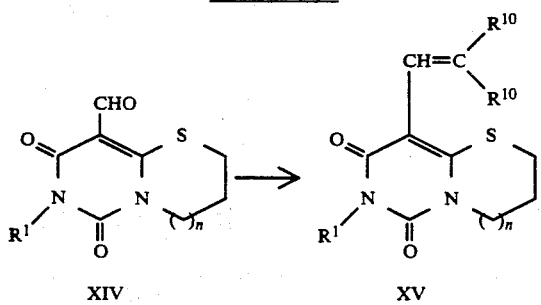

wherein $R^1$, $R^{10}$ and n have the same meanings as given above.

Reaction (n):

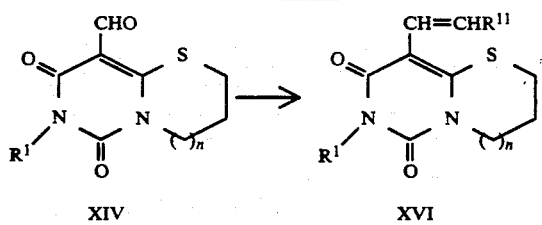

wherein $R^1$, $R^{11}$ and n have the same meanings as given above.

Reaction (o):

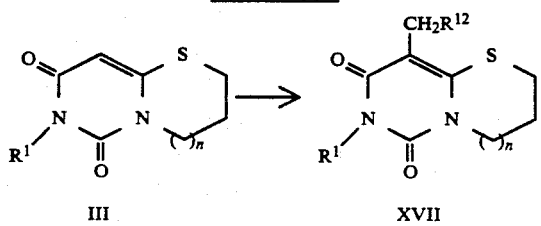

wherein $R^1$, $R^{12}$ and n have the same meanings as given above.

Reaction (p):

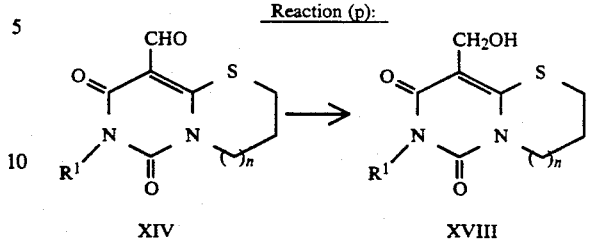

wherein $R^1$ and n have the same meanings as given above.

Reaction (q):

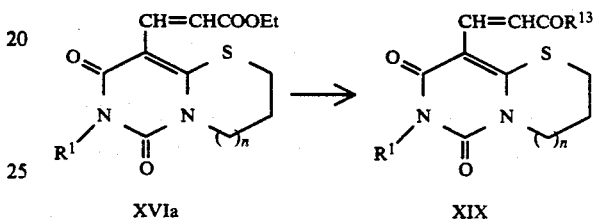

wherein $R^1$ and n have the same meanings as given above; $R^{13}$ represents a secondary amino group substituted by an alkyl group of 1 to 5 carbon atoms which may be substituted; and the substituent alkyl group may combine to form a cyclic group (such as piperidino, morpholino, piperazino or N'-phenylpiperazino).

Reaction (r):

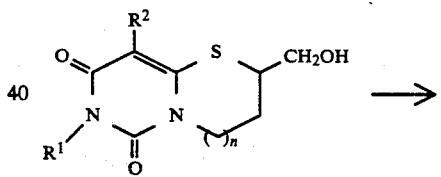

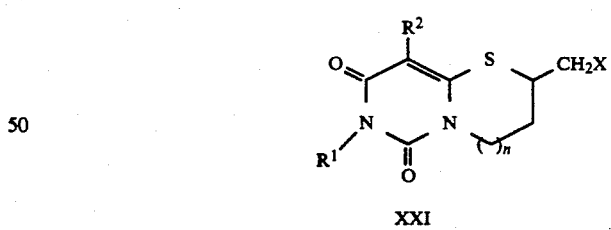

wherein $R^1$, $R^2$ and n have the same meanings as given above; and X represent chlorine.

Reaction (s):

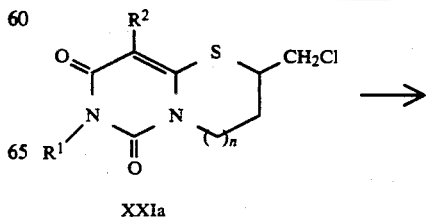

-continued

Reaction (s):

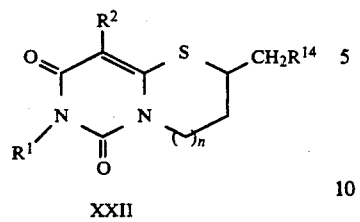

XXII wherein $R^1$, $R^2$ and n have the same meanings as given above; and $R^{14}$ represents an alkylthio group having about 1 to 4 carbon atoms or an arylthio group which may be substituted (such as alkyl of 1 to 4 carbon atoms, alkoxy of 1 to 4 carbon atoms or phenylthio which may be substituted by one or more halogen atoms).

Reaction (t):

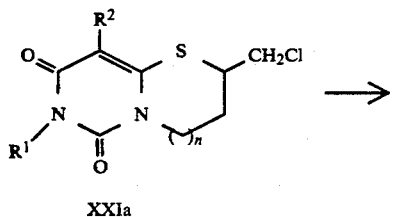

XXIa

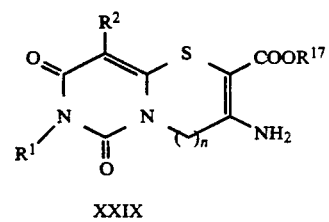

XXIII wherein $R^1$, $R^2$ and n have the same meanings as given above.

Reaction (u):

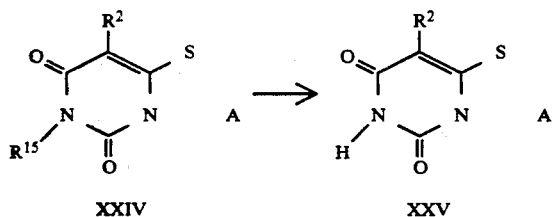

XXIV    XXV wherein $R^2$ and A have the same meanings as given above. $R^5$ represents a benzyl group which may be substituted.

Reaction (v):

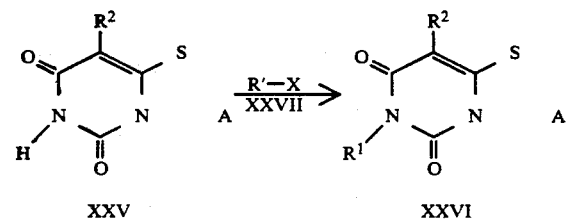

XXV    XXVI wherein $R^1$, $R^2$ and A have the same meanings as given above.

Reaction (w):

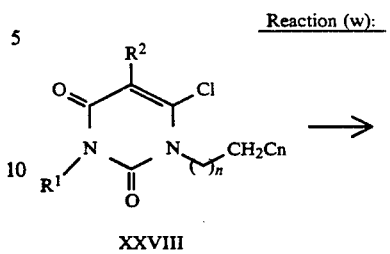

XXVIII

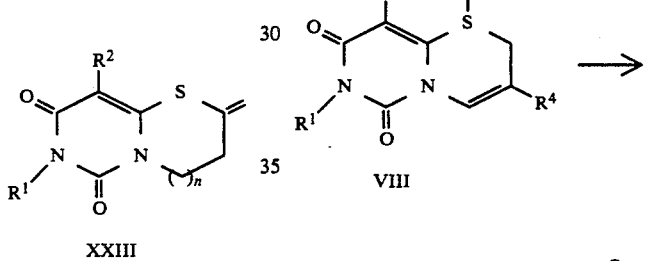

XXIX wherein $R^1$, $R^2$, $R^{17}$, A and n have the same meanings as given above.

Reaction (x):

VIII

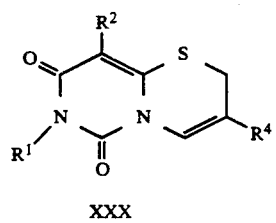

XXX wherein $R^1$, $R^2$ and $R^4$ have the same meanings as given above.

In the above-mentioned reaction (a), compound (II) is reacted with a sulfur reagent in an organic solvent to obtain compound (III).

As such organic solvents, there can be used aprotic solvents including carboxylic acid amides such as N,N-dimethylformamide, N,N-dimethylacetamide and N-methylpyrrolidone; sulfoxides such as dimethyl sulfoxide; ketones such as acetone, methyl ethyl ketone and methyl isobutyl ketone; and other solvents such as acetonitrile, ethylene glycol dimethyl ether, tetrahydrofuran and dioxane. In particular, the carboxylic acid amides and sulfoxides are preferably used.

Such sulfur reagents include sodium hydrosulfide (NaSH), sodium sulfide ($Na_2S$) and ammonium sulfide (($NH_4)_2S$). Sodium hydrosulfide is preferably used. Such a reagent is preferably used in an amount 2 to 4 times that of compound (II).

Further, this reaction is usually conducted at temperatures of 0°–30° C. for 0.5 to 10 hours. It is preferable to add sodium hydrosulfide to a solution of compound (II)

in N,N-dimethylformamide under ice cooling, followed by stirring at room temperature for about 1 to 2 hours.

In reaction (b), compound (III) is reacted with an oxidizing agent in an organic solvent to obtain compound (IV).

As such organic solvents, there can be used halogenated hydrocarbons such as dichloromethane, chloroform and dichloroethane; ethers such as ethyl ether, tetrahydrofuran and dioxane; and ketones such as acetone and methyl ethyl ketone. In particular, the halogenated hydrocarbons are preferably used.

Such oxidizing agents include organic peracids such as m-chloroperbenzoic acid; N-halocarboxylic acid amide such as N-bromosuccinic acid amide; and periodic acid. In particular, m-chloroperbenzoic acid is preferably used. Such a compound is preferably used in an amount slightly more than one equivalent in relation to compound (III).

Further, it is preferable that this reaction is conducted by adding m-chloroperbenzoic acid to a solution of compound (III) in methylene chloride little by little with stirring under ice cooling, followed by stirring at temperatures of 0°-30° C. for about 3 to 10 hours.

In reaction (c), compound (IV) is reacted with an oxidizing agent in an organic solvent to obtain compound (IV).

As such organic solvents, there can be used halogenated hydrocarbons such as dichloromethane, chloroform and dichloroethane; ethers such as ethyl ether, tetrahydrofuran and dioxan; and ketones such as acetone and methyl ethyl ketone. In particular, the halogenated hydrocarbons are preferably used.

Such oxidizing agents include organic peracids such as m-chloroperbenzoic acid; N-halocarboxylic acid amide such as N-bromosuccinic acid amide; and periodic acid. In particular, m-chloroperbenzoic acid is preferably used. Such a compound is preferably used in an amount slightly more than one equivalent of compound (IV).

Further, it is preferable that this reaction is conducted by adding m-chloroperbenzoic acid to a solution of compound (IV) in methylene chloride little by little with stirring under ice cooling, followed by stirring at temperatures of 0°-30° C. for about 5 to 20 hours.

In reaction (d), compound (IVa) is reacted with an acid anhydride in an organic solvent to obtain compound (VI).

As such organic solvents, there can be used halogenated hydrocarbons such as dichloromethane, chloroform and dichloroethane; ethers such as ethyl ether, tetrahydrofuran and dioxan; and ketones such as acetone and methyl ethyl ketone. The acid anhydrides used in the reaction can also be employed as solvents. In particular, the halogenated hydrocarbons such as dichloromethane and dichloroethane are preferably used.

Such acid anhydrides include acetic anhydride and trifluoroacetic anhydride can be used depending on their purpose. Such an acid anhydride is used in an amount usually 1 to 10 times, preferably 2 to 3 times that of compound (IVa). Further, this reaction is usually conducted at temperatures of 0°-30° C. for 5 to 30 hours. It is preferable to add the acid anhydride to a solution of compound (IVa) in dichloroethane, followed by stirring at room temperature for about 10 to 20 hours.

The reaction product thus obtained is a 2-o-acyl form in which $R^5$ is an acyl group such as acetyl and trifluoroacetyl. When an amine (for example, triethylamine) is allowed to exist in the reaction solution in an amount about 1 to 2 times that of the acid anhydride, a 2-hydroxy form in which $R^5$ is a hydrogen atom can be obtained. In this case, it is preferred that the reaction conditions are similar to those under which the 2-O-acyl form is obtained, except that the amine is used.

In reaction (e), compound (VI) is reacted in an organic solvent in the presence of an acid catalyst to obtain compound (VII).

As such organic solvents, there can be used aromatic hydrocarbons such as benzene, toluene and xylene; halogenated hydrocarbons such as dichloromethane, chloroform and dichloroethane; ethers such as ethyl ether, tetrahydrofuran and dioxan; and ketones and nitriles usually used as solvents. In particular, the aromatic hydrocarbons such as benzene and toluene are preferably used.

Such acid catalysts include sulfonic acids such as methanesulfonic acid, p-toluenesulfonic acid and trifluoromethanesulfonic acid; and other catalysts such as trichloroacetic acid and sulfuric acid. In particular, the sulfonic acids such as p-toluenesulfonic acid are preferably used. It is preferred that such an acid catalyst is used in a catalytic amount.

Further, this reaction is usually conducted at a temperature from room temperature up to the boiling point of the solvent used for about 3 to 30 hours. It is preferable to add a catalytic amount of p-toluenesulfonic acid to a solution of compound (VI) in toluene, followed by heating under reflux for about 4 to 7 hours.

Alternatively, compound (VII) may be obtained easily by conducting reactions (b), (d) and (e) serially under similar conditions as described above, without isolation of the reaction products (IV) and (VI).

In reaction (f), compound (VII) is reacted with an oxidizing agent in an organic solvent to obtain compound (VIII).

As such organic solvents, there can be used halogenated hydrocarbons such as dichloromethane, chloroform and dichloroethane; ethers such as ethyl ether, tetrahydrofuran and dioxane; and ketones such as acetone and methyl ethyl ketone. In particular, the halogenated hydrocarbons are preferably used.

Such oxidizing agents include peracids such as m-chloroperbenzoic acid; N-halocarboxylic acid amide such as N-bromosuccinic acid amide; and periodic acid. In particular, m-chloroperbenzoic acid is preferably used. Such a compound is preferably used in an amount slightly more than one equivalent of compound (VII).

Further, it is preferable that this reaction is conducted by adding m-chloroperbenzoic acid to a solution of compound (VII) in methylene chloride little by little with stirring under ice cooling, followed by stirring at temperatures of 0°-30° C. for about 3 to 10 hours.

In reaction (g), compound (VI) is reacted with a nucleophilic reagent in an organic solvent in the presence of an acid catalyst to obtain compound (IX).

As such organic solvents, there can be used halogenated hydrocarbons such as dichloromethane, chloroform and dichloroethane; and ethers such as tetrahydrofuran and dioxane. When alcohols such as methanol and ethanol or mercaptans are used as nucleophilic reagents, these compounds themselves can be used as solvents. In particular, the halogenated hydrocarbons such as dichloroethane are preferably used.

As such acid catalysts, there can be used organic acids such as acetic acid, trichloroacetic acid and p-toluene-sulfonic acid; and inorganic acids such as hydrogen chloride, sulfuric acid and boron trifluoride. The catalyst used for the reaction can be suitably changed depending on the nucleophilic reagent used.

The nucleophilic reagents include alcohols such as methanol and ethanol, and thiols such as ethyl mercaptan and thiophenol. Such a compound is used in an amount equivalent to compound (VI) or in large excess (when used as the solvent). However, the thiol is preferably used in an amount about 2 to 5 times that of compound (VI). Further, this reaction is conducted at temperatures of 0°-50° C. for about 10 hours to 3 days, preferably at room temperature for about 1 to 3 days.

In reaction (h), compound (IIIa) is reacted with a nitrating agent in a solvent to obtain compound (X).

Such a solvent is suitably changed depending on the nitrating agent used for the reaction.

The nitrating agents include various reagents, for example, so-called mixed acid prepared by combining nitric acid and sulfuric acid, acetyl nitrate, nitric acid, nitronium tetrafluoroborate ($NO_2^+BF_4^-$), nitrogen oxides ($NaNO_2$ and $N_2O_5$) and ethyl nitrate. Of these reagents, mixed acid is more preferable as the sure, inexpensive nitrating agent. When mixed acid is used as the nitrating agent, it is preferred to use the reagent itself as the solvent. Such a nitrating agent is used usually in large excess, preferably in an amount about 3 to 10 times that of compound (IIIa).

Further, this reaction is usually conducted at temperatures of 0°-30° C. for 0.5 to 3 hours. It is preferable to add fuming nitric acid to a solution of compound (IIIa) in concentrated sulfuric acid little by little under ice cooling so as to keep a reaction temperature at about 0° to 5° C., followed by stirring at a similar temperature for about 0.5 to 2 hours.

In reaction (i), the nitro group of compound (X) is reduced to an amino group by a reducing agent, and the resulting amino derivatives allowed to react with an organic carboxylic acid or an anhydride thereof, thereby obtaining compound (XI).

Such an organic solvent is suitable selected depending on the reducing agent used at that time.

The reducing agents include catalytic reducing agents which react in the presence of a palladium catalyst or the like, sulfur reducing agents such as sodium hydrosulfite ($Na_2S_2O_4$) and metals such as iron and zinc. In particular, when iron or zinc is used as the reducing agent, an alcohol such as methanol or ethanol used as the organic solvent may contain a suitable amount of an organic acid such as formic acid or acetic acid. The organic acid reacts with the amino group produced by reduction of the nitro group to form an acylamino derivative (X). In this case, the use of an organic acid as the solvent is more convenient and preferable.

Further, this reaction is usually conducted at a temperature around the boiling point of the solvent for about 3 to 20 hours. It is preferable to react compound (X) in the organic acid such as acetic acid for about 3 to 5 hours while heating under reflux in the presence of zinc in an amount of 3 to 5 times that of compound (X).

In reaction (j), compound (XI) is hydrolyzed in an organic solvent in the presence of an acid to obtain compound (XII).

Such organic solvents include alcohols such as methanol and ethanol, and ethers such as tetrahydrofuran and dioxane. In particular, the alcohols such as methanol and ethanol are preferably used.

As such acids, mineral acids such as hydrochloric acid and sulfuric acid are preferably used.

Further, this reaction is usually conducted at a boiling point of the solvent for about 2 to 10 hours. It is preferable to add a one-fifth to equivalent amount of 0.5 to 2 N-hydrochloric acid in relation to compound (XI) to an alcoholic solution of compound (XI) to conduct the reaction for about 2 to 5 hours.

In reaction (k), compound (XII) is alkylated by an alkylating agent in an organic solvent to obtain an alkylamino form (XIIIa), and acylated by an acylating agent in an organic solvent to obtain an acylamino form (XIIIb).

In alkylation reaction, as such organic solvents, there can be used aprotic solvents usually employed, including carboxylic acid amides such as N,N-dimethylformamide, N,N-dimethylacetamide and N-methylpyrrolidone; sulfoxides such as dimethyl sulfoxide; ketones such as acetone and methyl ethyl ketone; and other solvents such as acetonitrile. In particular, the carboxylic acid amides and sulfoxides are preferably used.

In reaction (l), compound (IIIa) is reacted with a formulating agent in an organic solvent to obtain compound (XIV).

Such an organic solvent varies depending on what compound is used as the formylating agent. The organic solvents include alcohols, ketones, halogenated hydrocarbons, ethers, esters, amides and sulfoxides which are usually used as solvents, but are not limited thereto.

Such formylating agents include Vilsmeier reagents (N,N- dimethylformamide-phosphorus oxychloride), acid anhydrides (formic acetic anhydride), ethyl formate-sodium ethoxide, chloroform-potassium hydroxide (Reimer-Tiemann reaction) and chloral ($Cl_3C$-CHO). In particular, the Vilsmeier reagents are preferably used. Such a formylating agent is preferably used in an amount more than one equivalent in relation to compound (IIIa). The Vilsmeier reagents (N,N-dimethylform- amide-phosphorus oxychloride) are preferably used in an amount of 1.5 to 3 equivalents.

Further, it is preferable that this reaction is conducted by adding the Vilsmeier reagent previously prepared to a solution of compound (IIIa) in N,N-dimethylformamide little by little with stirring under ice cooling so that the reaction temperature does not exceed about 40° C., followed by stirring at room temperature for about 2 to 5 hours.

In reaction (m), compound (XIV) is condensed with an active methylene compound in a solvent in the presence of a base to obtain compound (XV).

Such organic solvents include alcohols such as methanol and ethanol; ethers such as tetrahydrofuran and dioxane; and carboxylic acid amides such as dimethylformamide.

Further, such bases include potassium carbonate, sodium carbonate, sodium hydroxide, potassium hydroxide, sodium hydride and potassium t-butoxide.

Furthermore, such active methylene compounds include malonitrile, malonic esters and malonic acid amide.

It is preferable that the solvent and the base used for the reaction is suitably selected depending on the active methylene compound reacted at that time.

Moreover, this reaction is usually conducted at a temperature of about 50° C. to the boiling point of the solvent for about 5 to 20 hours.

In reaction (n), compound (XIV) is reacted with a Wittig reagent in an organic solvent to obtain compound (XVI).

Such organic solvents include halogenated hydrocarbons such as dichloromethane, chloroform and dichloroethane; ethers such as ethyl ether, tetrahydrofuran and dioxane; aromatic hydrocarbons such as benzene and toluene; and alcohols such as methanol and ethanol.

Further, such Wittig reagents include stabilized phosphoranes, semi-stabilized phosphoranes and unstabilized phosphoranes such as carboethoxymethylenetriphenylphosphorane, cyanomethylenetriphenylphosphorane, pentylenetriphenylphosphorane and benzylidenetriphenylphosphorane.

Furthermore, this reaction is usually conducted at a temperature of about 50° C. to the boiling point of the solvent for about 5 to 20 hours. It is preferable to heat compound (XIV) and the Wittig reagent under reflux in an appropriate solvent for about 5 to 10 hours.

In reaction (o), compound (III) is aminomethylated by the reaction of formaldehyde and an amine, namely the Mannich reaction to obtain compound (XVII).

Such organic solvents include alcohols such as methanol and ethanol; ethers such as tetrahydrofuran and dioxane; halogenated hydrocarbons such as dichloroethane, carbon tetrachloride and chloroform; and other usual solvents such as acetonitrile and acetic acid.

As Mannich reagents, there can be used appropriate combinations of paraformaldehyde or formic acid with secondary amines (for example, dimethylamine hydrochloride, diethylamine hydrochloride, piperidine, morpholine, piperazine and salts thereof. Such a compound is preferably used in an amount 2 to 5 times that of compound (III).

Further, it is preferable that this reaction is usually conducted by heating compound (III) and the Mannich reagent in the suitable solvent at a temperature around the boiling point of the solvent for about 10 to 20 hours.

In reaction (p), compound (XIV) is reacted with a reducing agent in a solvent.

Such organic solvents include alcohols such as methanol and ethanol; and ethers such as ethyl ether, tetrahydrofuran and dioxane.

Such reducing agent include metal hydride complex compounds such as sodium borohydride and aluminium lithium hydride, and tributyltin hydrides and are preferably used in an amount 2 to 4 times that of compound (XIV).

It is preferable that the reaction is conducted at temperatures of 0°-30° C. for 0.5 to 2 hours after addition of sodium borohydride to a solution of the compound (XIV) in alcohol.

In reaction (q), compound (XVIa) is reacted in an aprotic solvent with a dimethylaluminum amide derivative obtained by reacting a primary or secondary amine with trimethylaluminium according to the method described in the literature [A. Basha S, *Tetrahedron Lett.* 48, 4171 (1977)].

As such aprotic solvents, there can be used halogenated hydrocarbons such as dichloromethane, chloroform and dichloroethane; and ethers such as ethyl ether, tetrahydrofuran and dioxane. In particular, halogenated hydrocarbons such as dichloromethane and dichloroethane are preferably used.

The synthesis of the dimethylamide is conducted by adding a solution of trimethylaluminium in hexane to the amine (for example, an alkyl amine, an aryl amine, morpholine, piperidine and N-phenylpiperazine) in the solvent such as methylene chloride, chloroform or dichloroethane in a stream of nitrogen to form the dimethylaluminum amide form.

It is preferable that this reaction is usually conducted by adding a solution of compound (XVIa) in the same solvent as used in the preparation of the dimethylaluminum amide form, such as methylene chloride, little by little with stirring at temperatures of 0°-30° C., and then heating the mixture under reflux for about 10 to 30 hours.

After the reaction is completed, the unreacted aluminum reagent is decomposed with hydrochloric acid, and then the reaction product thus obtained can be easily isolated and purified by methods known in the art.

In reaction (r), compound (XX) is reacted with a halogenating reagent in an organic solvent to obtain compound (XXI).

As such organic solvents, there are preferably used aprotic solvents including halogenated hydrocarbons such as dichloromethane, chloroform and dichloroethane; and ethers such as ethyl ether, tetrahydrofuran and dioxane.

Further, as such halogenating reagents, there can be used thionyl chloride, phosphorus oxychloride, phosphorus trichloride and phosphorus pentachloride. In particular, thionyl chloride is preferably used because of easy treatments after the reaction. As to this reaction, it is preferable to add the halogenating reagent such as thionyl chloride to a solution of compound (XX) in dichloromethane or dichloroethane little by little at temperatures of 0° C.-30° C., followed by heating under reflux for about 5 to 20 hours.

In reaction (s), compound (XXIa) is reacted with a nucleophilic reagent in an organic solvent to obtain compound (XXII).

As such organic solvents, there can be used halogenated hydrocarbons such as dichloromethane, chloroform and dichloroethane; ethers such as ethyl ether, tetrahydrofuran and dioxane; alcohols such as methanol, ethanol and methyl cellosolve; and carboxylic acid amides such as dimethylformamide. It is preferable that the solvent used is suitably selected depending on the nucleophilic reagent used.

Such nucleophilic reagents include thiols such as thiophenols and methyl mercaptan; alcohols such as methanol and ethanol; and amines such as alkyl amines, aralkyl amines and aromatic amines.

This reaction is preferably conducted in the presence of an appropriate base such as potassium carbonate, sodium carbonated or sodium hydride.

With respect to this reaction, it is preferred to react compound (XXIa) in the solvent such as ethanol in the presence of the base such as potassium carbonate at a temperature from room temperature up to the boiling point of the solvent for about 5 to 50 hours.

In reaction (t), compound (XXIa) is reacted with a base in an organic solvent to obtain compound (XXIII).

As such organic solvents, there can be used halogenated hydrocarbons such as dichloromethane, chloroform and dichloroethane; ethers such as ethyl ether, tetrahydrofuran and dioxane; alcohols such as methanol and ethanol; carboxylic acid amides such as dimethylformamide; and amines such as pyridine.

As such bases, there can be used amines such as triethylamine, pyridine and piperidine; and alkali salts such as potassium t-butoxide, sodium hydride, potassium carbonate and sodium carbonate. It is preferable that the base is suitably selected depending on the solvent used.

Further, it is preferable that this reaction is usually conducted at temperatures of room temperature up to the boiling point of the solvent for about 5 to 50 hours.

After the reaction is completed, the reaction product thus obtained can be easily isolated and purified by recrystalization and column chromatography.

In reaction (u), compound (XXIV) is reacted with a debenzylating agent in an organic solvent to obtain compound (XXV).

As such organic solvents, there can be used aromatic hydrocarbons such as benzene, toluene and xylene; and halogenated hydrocarbons such as dichloromethane, chloroform and dichloroethane. In particular, benzene, toluene and xylene are preferable.

As such debenzylating agents, there can be used boron tribormide, metal natrium-liq. ammonia and catalytic reduction, among them $BBr_3$ is preferable for its simplicity. Such compounds may be added in an amount of about 2 to 10 moles, preferably 2 to 5 moles to 1 mole of compound (XXIV).

Further, it is preferable that this reaction is usually conducted by adding $BBr_3$ to a suspension of the compound (XXIV) in toluene at a temperature from 50° C up to the boiling point of the solvent for about 5 to 40 hours, preferably around the boiling point of the solvent for 10 to 20 hours.

In reaction (v), compound (XXV) is reacted with an alkylating agent (XXVII) in an organic solvent in the presence of base to obtain compound (XXVI).

As such organic solvents, there can be used dimethylformamide, dimethylacetamide, dimethylsulfoxide, acetonitrile, acetone and ethylmethylketone.

As such bases, there can be used sodium hydride, potassium t-butoxide, potassium carbonate and sodium carbonate.

As such alkylating agents (XXVII), there can be used substituted halides such as chloride, bromide and iodide.

Further, it is preferable that this reaction is usually conducted by employing about 1 to 3 moles of potassium carbonate and about 1 to 3 moles of alkylating agent (XXVII) to 1 mole of compound (XXV) in dimethylformamide at a temperature from room temperature up to the boiling point of the solvent for about 5 to 40 hours, preferably around 50° to 100° C. for 10 to 20 hours.

In reaction (w), compound (XXVIII) is reacted with thioglycolate in an organic solvent in the presence of base to obtain compound (XXIX).

As such organic solvents, there can be used alcohols such as methanol, ethanol and propanol; and amides such as dimethylformamide and dimethylacetamide.

As such bases, there can be used potassium carbonate, sodium carbonate, sodium hydride and potassium t-butoxide.

Further, it is preferable that this reaction is usually conducted by employing about 2 to 4 moles of thioglycolate and about 2 to 4 moles of potassium carbonate per 1 mole of compound (XXVIII) in ethanol at a temperature around the boiling point of the solvent for about 10 to 20 hours.

In reaction (X), compound (VIII) is reacted with a reducing agent in an organic solvent to obtain compound (XXX).

Such reducing agents include metal hydride complex compounds such as sodium borohydride and aluminium lithium hydride; halogenated phosphorous compounds like phosphorus trichloride; titanium trichloride and silicon trichloride, and phosphorus trichloride is preferable for its simplicity. As solvents, there can be used amides such as dimethylformamide and dimethylacetamide; and halogenated hydrocarbons such as dichloroethane and chloroform, and among them dimethylformamide is preferable.

Further, it is preferable that this reaction is usually conducted by adding about 2 to 5 moles of phosphorus trichloride to 1 mole of compound (VIII) in DMF and mixing at a temperature from about −20° C. to room temperature for about 30 minutes to 1 hour.

After the reaction is completed, the reaction product thus obtained can be easily isolated and purified by conventional methods such as column chromatography and recrystalization.

In reactions (a) to (x), the starting compounds (II) and (XVIII) can be prepared by the following method.

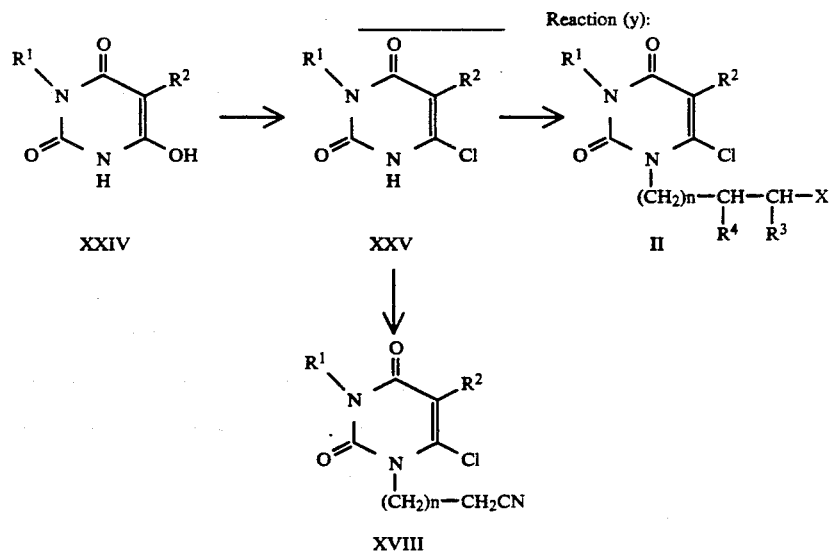

(wherein each symbol has the same meaning as above given)

The starting compounds (II) can be easily obtained by reacting the compounds (XXV) synthesized by or in accordance with the methods described in Chem. Ber. 95, 1597 (1962) and Ann. Chem. 691, 142 (1966) with various alkyl dihalides (such as 1-bromo-2-chloroethane, 1-bromo-3-chloropropane, 1-bromo-4-chlorobutane and 1-bromo-3-chloro-2-methylpropane) in an aprotic solvent such as dimethylformamide in the presence of potassium carbonate or sodium carbonate at a temperature of 50° to 100° C. for about 10 to 20 hours.

REFERENCE EXAMPLE 1

6-Chloro-5-phenyl-3-propylpyrimidine-2,4(1H,3H)-dione

Phosphorus oxychloride (500 ml) was added dropwise to 50% ethanol (100 ml) with stirring at room temperature. 5-Phenyl-3-propylpyrimidine-2,4,6(1H,3H)-trione (107 g) was added to the solution little by little with stirring. The reaction solution was heated at 50° C. for 30 minutes, followed by heating under reflux for 4 hours. The reaction solution was concentrated under reduced pressure to dryness. The resulting syrup was poured on ice water little by little, and stirred for a while. The precipitated crystals were collected by filtration, washed with water, and then dried. Recrystallization from DMF (500 ml)-water (100 ml) gave colorless plates (73 g, 63%), m.p. 230°-231° C.

REFERENCE EXAMPLES 2-7

The following compounds were synthesized by methods similar to that of Reference Example 1.

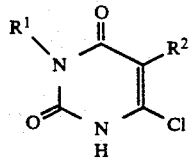

| Reference Example No. | R¹ | R² | Yield (%) | Melting Point (°C.) |
|---|---|---|---|---|
| 2 | Me | Ph | 45 | 295-300 |
| 3 | Et | Ph | 71 | 220-223 |
| 4 | Pr | H | 71 | 196-200 |
| 5 | Bu | Ph | 75 | 205-208 |
| 6 | Ph | Ph | 44 | >300 |
| 7 | Bzl | Ph | 66 | 271-280 |

REFERENCE EXAMPLE 8

6-Chloro-1-(3-chloroethyl)-5-phenyl-3-propylpyrimidine-2,4(1H,3H)-dione

1-Bromo-3-chloroethane (3 ml) and potassium carbonate (3.48 g) were added to a solution of 6-chloro-5-phenyl-3-propylpyrimidine-2,4(1H,3H)-dione (4 g) in DMF (40 ml), and the mixture was stirred at 50° C. for 20 hours. The reaction solution was concentrated to dryness. A resulting residue was dissolved in chloroform and H₂O, and the organic layer was washed with water and dried. The solvent was evaporated to dryness to give a syrup, which was purified by column chromatography on silica gel. Recrystallization of the crude crystals from methylene chloride-hexane gave colorless prisms (4 g, 63%), mp 93°-94° C.

REFERENCE EXAMPLES 9 TO 42

The following compounds were synthesized by methods similar to that of Reference Example 8.

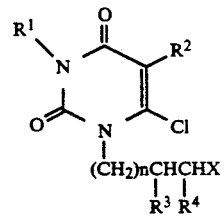

| Reference No. | R¹ | R² | R³ | R⁴ | n | x | Yield (%) | m.p. (°C.) |
|---|---|---|---|---|---|---|---|---|
| 9 | Me | H | H | H | 0 | Cl | 43 | 105-106 |
| 10 | Me | Ph | H | H | 0 | Cl | 62 | 138-140 |
| 11 | Et | H | H | H | 0 | Cl | 63 | 93-94 |
| 12 | Et | Ph | H | H | 0 | Cl | 71 | 123-127 |
| 13 | Pr | H | H | H | 0 | Cl | 78 | Syrup |
| 14 | Pr | Ph | H | H | 0 | Cl | 94 | Syrup |
| 15 | Bu | H | H | H | 0 | Cl | 81 | Syrup |
| 16 | Bu | Ph | H | H | 0 | Cl | 82 | Syrup |
| 17 | Ph | Ph | H | H | 0 | Cl | 50 | 163-165 |
| 18 | Me | H | H | H | 1 | Cl | 59 | Syrup |
| 19 | Me | Ph | H | H | 1 | Cl | 83 | Syrup |
| 20 | Et | H | H | H | 1 | Cl | 83 | Syrup |
| 21 | Et | H | H | Me | 1 | Br | 56 | Syrup |
| 22 | Et | H | Me | H | 1 | Cl | 77 | Syrup |
| 23 | Et | Ph | H | H | 1 | Cl | 100 | Syrup |
| 24 | Pr | H | H | H | 1 | Cl | 75 | Syrup |
| 25 | Pr | H | H | Me | 1 | Br | 47 | Syrup |
| 26 | Pr | H | Me | H | 1 | Cl | 74 | Syrup |
| 27 | Pr | Ph | H | H | 1 | Cl | 90 | Syrup |
| 28 | Pr | Ph | Me | H | 1 | Cl | 75 | Syrup |
| 29 | Bu | H | H | H | 1 | Cl | 73 | Syrup |
| 30 | Bu | Ph | H | H | 1· | Cl | 93 | Syrup |
| 31 | Bzl | H | H | H | 1 | Cl | 96 | Syrup |
| 32 | Ph | H | H | H | 1 | Cl | 85 | Syrup |
| 33 | Ph | Ph | H | H | 1 | Cl | 80 | Syrup |
| 34 | Me | H | H | H | 2 | Cl | 64 | Syrup |
| 35 | Et | H | H | H | 2 | Br | 48 | Syrup |
| 36 | Pr | H | H | H | 2 | Cl | 69 | Syrup |
| 37 | Pr | Ph | H | H | 2 | Cl | 87 | Syrup |
| 38 | Bu | H | H | H | 2 | Cl | 78 | Syrup |
| 39 | Pr | NO₂ | H | H | 0 | Cl | 99 | Syrup |
| 40 | Pr | NO₂ | H | H | 1 | Cl | 98 | Syrup |
| 41 | Pr | NO₂ | H | H | 2 | Cl | 98 | Syrup |
| 42 | Bzl | Ph | H | H | 1 | Cl | 67 | Syrup |

REFERENCE EXAMPLE 43

6-Chloro-1-cyanomethyl-3-propylpyrimidine-2,4(1H,3H)-dione

Chloroactonitrile (16.5 g) and potassium carbonate (29.3 g) were added to a solution of 6-chloro-3-propylpyrimidine-2,4(1H,3H)-dione (20 g) in DMF (200 ml), and the mixture was stirred at room temperature for 24 hours. The reaction solution was concentrated and evaporated to dryness to obtain a residue. A resulting residue was dissolved in chloroform and H₂O, and the organic layer was washed with water and dried. The solvent was evaporated to dryness to give a syrup, which was purified by column chromatography on silica gel to give a crystalline product. Recrystalization of the crude crystals from ethyl acetate-isopropylether gave colorless prisims (21.1 g, 87%), mp. 83°-84° C.

REFERENCE EXAMPLE 44

6-Chloro-1-cyanomethyl-5-phenyl-3-propylpyrimidine-2,4(1H,4H)-dione

The captioned compound was synthesized by methods similar to that of Reference Example 43.

M.p. 194°–195° C.

The sulfur-containing fused pyrimidine derivatives (compounds (I)) represented by general formula (I) and the salts thereof according to the present invention have inhibitory activities on vasoconstriction, bronchus smooth muscle constriction and the activity of reducing the infarct size in ischemic and reperfused heart to mammals including humans, and therefore are useful as therapeutic and ameliorative agents for myocardial infarction, angina pectoris and asthma. Compounds (I) and the salts thereof have also inhibitory activities on IL-1 production, anti-inflammatory activity, antipyretic activity and analgesic activity, and therefore are useful as therapeutic and ameliorative agents for rheumatoid arthritis, lumbago, cervico-omo-brachial syndrome and scabies. Further, the compounds are useful for treatment of cerebral lesions and memory impairment (for example, Alzheimer's disease) through inducing the production of NGF.

The toxicity of compounds (I) is low. Hence, compounds (I) of the present invention or a salt thereof, when used as pharmaceutical drugs, can be safely administered parenterally or orally in the forms of powders, granules, tablets, capsules, injections, suppositories and ointments, solely or in combination with pharmaceutically acceptable additional components, such as vehicles, disintegrators, lubricants, binders, dispersants, plasticizers or diluents.

The dosage is dependent on the type of disease to be treated, the symptom of the disease, the subject to whom the drugs are administered and the method of administration. For example, when orally administered to adult patients with myocardial infarction or angina pectoris, it is advantageous that the active ingredients (compounds (I)) are normally administered in one dose of about 0.1 to 30 mg/kg of weight, preferably about 0.5 to 10 mg/kg of weight, about once to 3 times a day.

Of the sulfur-containing fused pyrimidine derivatives represented by general formula (I) and the salts thereof according to the present invention, pyrimido[6,1-b][1,3]thiazepin-7,9(8-H)-diones are novel in their skeleton itself as described above. It is industrially extremely useful to provide these structurally novel compounds.

The present invention will be described in detail with the following Examples, Preparation Examples and Experimental Examples. It is understood of course that these are not intended to limit the scope of the invention.

In this specification, the following abbreviations are used.

Me: methyl, Et: ethyl, Pr: propyl, Bu: butyl,
All: allyl, Bzl: benzyl, Ph: phenyl, Ac: acetyl,
s: singlet, d: Doublet, t: Triplet, q: quartet,
m: multiplet, brs: broad signal.

EXAMPLE 1

9-Phenyl-7-propyl-3,4-dihydro-2H,6H-pyrimido[6,1-b][1,3] thiazine-6,8(7H)-dione Sodium hydrosulfide (3.3 g) was added to a solution of 6-chloro-1-(3-chloropropyl)-5-phenyl-3-propyluracil (7 g) in DMF (60 ml) little by little under ice cooling and the mixture was stirred for 1 hour. The reaction solution was concentrated to dryness. The residue was dissolved in methylene chloride-H$_2$O, and the organic layer was washed with water and dried. The solvent was evaporated and the resulting crude crystals were recrystallized from methanol to give colorless crystals (3.85 g, 62%).

Melting point: 132°–133° C.

| | Elemental analysis for C$_{16}$H$_{18}$N$_2$O$_2$S: | | |
|---|---|---|---|
| | C (%) | H (%) | N (%) |
| Calcd: | 63.55; | 6.00; | 9.26 |
| Found: | 63.59; | 6.05; | 9.23 |

$^1$H-NMR(CDCl$_3$)δ: 0.94(3H,t),1.42–1.93(2H,m), 2.02–2.37(2H,m),2.92(2H,t),3.94(2H,t), 4.08(2H,t),7.08–7.50(5H,m)

EXAMPLES 2 TO 36

The following compounds were synthesized by methods similar to that of Example 1.

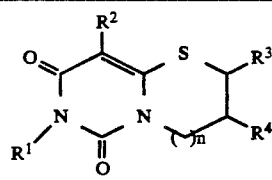

| Example No. | R$^1$ | R$^2$ | R$^3$ | R$^4$ | n | Yield (%) | mp (°C.) | $^1$H-NMR(δ) (90 MHz)δ |
|---|---|---|---|---|---|---|---|---|
| 2 | Me | H | H | H | 0 | 61 | 147–148 | (CDCl$_3$); 3.26(3H, s), 3.35(2H, t), 4.32(2H, t), 5.68(1H, s). |
| 3 | Me | Ph | H | H | 0 | 55 | 215–217 | (CDCl$_3$); 3.24(2H, t), 3.35(3H, s), 4.41(2H, t), 7.36(5H, s). |
| 4 | Et | H | H | H | 0 | 72 | 124–125 | (CDCl$_3$); 1.19(3H, t), 3.37(2H, t), 4.33(2H, t), 3.93(2H, q), 5.67(1H, s). |
| 5 | Pr | H | H | H | 0 | 69 | 137–139 | (CDCl$_3$); 0.92(3H, t), 1.40–1.85(2H, m), 3.36(2H, t), 3.83(2H, q), 4.31(2H, t), 5.65(1H, s). |
| 6 | Pr | Ph | H | H | 0 | 55 | 128–129 | (CDCl$_3$); 0.93(3H, t), |

-continued

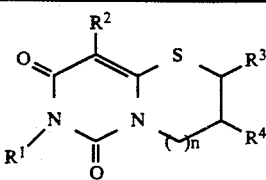

| Example No. | R¹ | R² | R³ | R⁴ | n | Yield (%) | mp (°C.) | ¹H-NMR(δ) (90 MHz)δ |
|---|---|---|---|---|---|---|---|---|
| | | | | | | | | 1.46–1.91(2H, m), 3.20(2H, t), 3.91(2H, t), 4.37(2H, t), 7.38(5H, s). |
| 7 | Bu | H | H | H | 0 | 70 | 121–123 | (CDCl₃); 0.92(3H, t), 1.10–1.85(4H, m), 3.35(2H, t), 3.90(2H, t), 4.31(2H, t). |
| 8 | Bu | Ph | H | H | 0 | 64 | 123–124 | (CDCl₃); 0.92(3H, t), 1.13–1.85(4H, m), 3.22(2H, t), 3.93(2H, t), 4.40(2H, t), 7.39(5H, s). |
| 9 | All | H | H | H | 0 | 55 | 126–129 | (CDCl₃); 3.35(2H, t), 4.31(2H, t), 4.47(2H, d), 5.02–5.37(2H, m), 5.67(1H, s), 5.63(1H, m). |
| 10 | Ph | H | H | H | 0 | 86 | 226–228 | (d₆-DMSo); 3.45(3H, t), 4.23(3H, t), 5.84(1H, s), 7.10–7.60(5H, m). |
| 11 | Ph | Ph | H | H | 0 | 78 | 231–232 | (CDCl₃); 3.26(2H, t), 4.43(2H, t), 7.16–7.56(10H, m). |
| 12 | Me | H | H | H | 1 | 67 | 153–154 | (CDCl₃); 2.08–2.41(2H, m), 3.06(2H, t), 4.00(2H, t), 3.32(3H, s), 5.71(1H, s). |
| 13 | Me | Ph | H | H | 1 | 51 | 157–159 | (CDCl₃); 1.99–2.35(2H, m), 2.92(2H, t), 4.09(2H, t), 3.40(3H, s), 7.13–7.55(5H, m). |
| 14 | Et | H | H | H | 1 | 71 | 142–143 | (CDCl₃); 1.00(3H, t), 2.09–2.41(2H, m), 3.08(2H, t), 3.97(2H, q), 4.01(2H, t), 5.69(1H, s). |
| 15 | Et | H | H | Me | 1 | 46 | 97–98 | (CDCl₃); 1.19(3H, t), 1.40(3H, d), 1.60–2.07(1H, m), 2.22–2.55(1H, m), 3.29–3.80(2H, m), 3.95(2H, q), 4.27–4.53(1H, m), 5.63(1H, s). |
| 16 | Et | H | Me | H | 1 | 67 | 73–75 | (CDCl₃); 1.19(3H, t), 1.20(3H, d), 2.04–2.52(1H, m), 2.61–3.39(3H, m), 3.96(2H, q), 4.21–4.42(1H, m), 5.69(1H, s). |
| 17 | Et | Ph | H | H | 1 | 60 | 141–143 | (CDCl₃); 1.27(3H, t), 2.03–2.35 (2H, m), 2.91(2H, t), 4.02(2H, q), 4.08(2H, t), 7.10–7.53(5H, m). |
| 18 | Pr | H | H | H | 1 | 55 | 83–85 | (CDCl₃); 0.93(3H, t), 1.40–1.90(2H, m), 2.10–2.40(2H, m), 3.09(2H, t), 3.75–4.10(4H, m), 5.71(1H, s). |
| 19 | Pr | H | Me | H | 1 | 26 | 93–94 | (CDCl₃); 0.92(3H, t), 1.41(3H, d), 1.39–2.06(3H, m), 2.21–2.56(1H, m), 3.28–3.70(2H, m), 4.25–4.56(1H, m), 5.63(1H, s). |
| 20 | Pr | H | H | Me | 1 | 32 | 87–88 | (CDCl₃); 0.92(3H, t), 1.17(3H, d), 1.42–1.87(2H, m), 2.06–2.52(1H, m), 2.59–3.42(2H, m), 3.86(3H, t), 4.21–4.46(1H, m), 5.67(1H, s). |
| 21 | Pr | Ph | H | Me | 1 | 61 | 118–119 | |
| 22 | Bu | H | H | H | 1 | 58 | 73–75 | (CDCl₃); 0.93(3H, t), 1.10–1.90(4H, m), 2.00–2.40(2H, m), 2.92(2H, t), 3.96(2H, t), 4.10(2H, t). |
| 23 | Bu | Ph | H | H | 1 | 43 | 123–126 | (CDCl₃); 0.93(3H, t), 1.04–1.84(4H, m), 2.02–2.34(2H, m), 2.91(2H, t), 3.97(2H, t), 4.07(2H, t), 7.12–7.53(5H, m). |
| 24 | Bzl | H | H | H | 1 | 55 | 142–143 | (CDCl₃); 1.99–2.32(2H, m), 2.99(2H, t), 3.93(2H, t), 5.09(2H, s), 5.71(1H, s), 7.10–7.56(5H, m). |
| 25 | Ph | H | H | H | 1 | 66 | 186–188 | (d₆-DMSO); 2.0–2.3(2H, m), 3.10(2H, t), 3.86(2H, m), 5.71(1H, s), 7.10–7.60(5H, m). |
| 26 | Ph | Ph | H | H | 1 | 59 | 217–219 | (CDCl₃); 2.06–2.38(2H, m), 2.95(2H, t), 4.09(2H, t), 7.15–7.47(10H, m). |
| 27 | Me | H | H | H | 2 | 33 | 68–69 | (CDCl₃); 1.70–2.20(4H, m), 2.99(2H, t), 3.31(3H, s), |

-continued

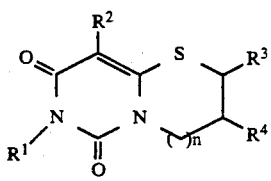

| Example No. | R¹ | R² | R³ | R⁴ | n | Yield (%) | mp (°C.) | ¹H-NMR(δ) (90 MHz)δ |
|---|---|---|---|---|---|---|---|---|
| 28 | Et | H | H | H | 2 | 30 | 78–79 | (CDCl₃); 1.27(3H, t), 1.69–2.20(4H, m), 2.99(2H, t), 4.37(2H, t), 3.96(2H, q), 4.38(2H, t), 6.06(1H, s). 6.03(1H, s). |
| 29 | Pr | H | H | H | 2 | 42 | 69–70 | (CDCl₃); 0.93(3H, t), 1.40–2.10(6H, m), 2.80–3.05(2H, m), 3.86(2H, t), 4.26–4.50(2H, m). |
| 30 | Pr | Ph | H | H | 2 | 54 | 136–138 | (CDCl₃); 0.94(3H, t), 1.48–2.11(6H, m), 2.85(2H, t), 3.94(2H, t), 4.45(2H, t), 7.11–7.48(5H, m). |
| 31 | Bu | H | H | H | 2 | 52 | 30–35 | (CDCl₃); 0.93(3H, t), 1.10–2.20(8H, m), 2.80–3.30(2H, m), 3.90(2H, t), 4.26–4.46(2H, m), 6.04(1H, s). |
| 32 | Pr | NO₂ | H | H | 0 | 47 | 189–191 | (CDCl₃); 0.93(3H, t), 1.43–1.90(2H, m), 3.40(2H, t), 3.88(2H, t), 4.57(2H, t). |
| 33 | Pr | NO₂ | H | H | 1 | 40 | 123–124 | (CDCl₃); 0.93(3H, t), 1.38–1.90(2H, m), 2.15–2.49(2H, m), 3.13(2H, t), 3.92(2H, t), 4.14(2H, t). |
| 34 | Pr | NO₂ | H | H | 2 | 23 | 109–110 | (CDCl₃); 0.94(3H, t), 1.40–2.23(6H, m), 3.08(2H, t), 3.91(2H, t), 4.43(2H, t). |
| 35 | Pr | H | CH₂OH | H | 0 | 52 | 103–104 | (CDCl₃); 0.91(3H, t), 1.39–1.84(2H, m), 3.60–4.05(5H, m), 4.20(1H, q), 4.43(1H, q), 5.66(1H, s). |
| 36 | Bzl | Ph | H | H | 1 | 60 | 155–157 | (CDCl₃); 2.12–2.28(2H, m), 2.92(2H, t), 4.07(2H, t), 5.16(2H, s) 7.21–7.60(10H, m) |

EXAMPLE 37

1-Oxo-9-phenyl-7-propyl-3,4-dihydro-2H,6H-pyrimido[6,1-b][1,3]thiazine-6,8(7H)-dione m-Chloroperbenzoic acid (3.78 g) was added to a solution of 9-phenyl-7-propyl-3,4-dihydro-2H,6H-pyrimido[6,1-b][1,3]thiazone-6,8(7H)-dione (6 g) in methylene chloride (90 ml) little by little with stirring under ice cooling and the mixture was stirred under ice cooling for 6 hours. The insoluble material was removed by filtration, and the filtrate was washed with an aqueous sodium bicarbonate. After drying, it was concentrated to dryness. The residue was purified by column chromatography on silica gel. The resulting crude crystals were recrystallized from methylene chyloride-isopropyl ether to give colorless needles (5.7 g, 90%).

Melting point: 190°–192° C.

| Elemental analysis for C₁₆H₁₈N₂O₃S: | | | |
|---|---|---|---|
| | C (%) | H (%) | N (%) |
| Calcd: | 60.36; | 5.70; | 8.80 |
| Found: | 59.93; | 5.67; | 8.42 |

¹H-NMR(CDCl₃)δ: 0.94(3H,t),1.47–1.92(2H,m), 2.00–2.89(3H,m),3.09–3.44(1H,m), 3.96(2H,t),4.09–4.82(2H,m),7.39(5H,s)

EXAMPLES 38 TO 57

The following compounds were synthesized by methods similar to that of Example 37.

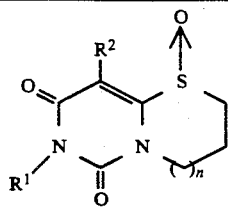

| Example No. | R¹ | R² | n | Yield (%) | m.p. (°C.) | ¹H-NMR($\delta$) |
|---|---|---|---|---|---|---|
| 38 | Me | Ph | 0 | 64 | 169–172 | (CDCl$_3$); 2.75–3.34(2H, m), 3.38(3H, s), 4.63–4.92(2H, m), 7.35–7.60(5H, m). |
| 39 | Et | Ph | 0 | 70 | 164–166 | (CDCl$_3$); 1.25(3H, t), 2.73–3.14(1H, m), 3.20–3.47(1H, m), 4.05(2H, q), 4.51–5.00(2H, m), 7.35–7.65(5H, m). |
| 40 | Bu | Ph | 0 | 82 | 175–177 | (CDCl$_3$); 0.95(3H, t), 1.13–1.85(4H, m), 2.75–3.15(1H, m), 3.21–3.48(1H, m), 3.99(2H, t), 4.52–4.89(2H, m), 7.35–7.63(5H, m). |
| 41 | Ph | Ph | 0 | 64 | 292–293 | (DMSO-d$_6$); 3.08–3.81(2H, m), 4.25–4.94(2H, m), 7.17–7.74(10H, m). |
| 42 | Me | Ph | 1 | 68 | 204–207 | (CDCl$_3$); 2.07–2.88(3H, m), 3.10–3.40(1H, m), 3.40(3H, s), 4.13–4.77(2H, m), 7.21–7.52(5H, m). |
| 43 | Et | Ph | 1 | 56 | 212–214 | (CDCl$_3$); 1.26(3H, t), 2.07–2.90(3H, m), 3.10–3.44(1H, m), 4.06(2H, q), 4.10–4.81(2H, m), 7.39(5H, s). |
| 44 | Pr | Ph | 1 | 90 | 190–192 | (CDCl$_3$); 0.94(3H, t), 1.47–1,92(2H, m), 2.00–2.89(3H, m), 3.09–3.44(1H, m), 3.96(2H, t), 4.09–4.82(2H, m), 7.39(5H, s). |
| 45 | Bu | Ph | 1 | 72 | 142–144 | (CDCl$_3$); 0.94(3H, t), 1.06–1.85(4H, m), 2.02–2.93(3H, m), 3.13–3.48(1H, m), 4.01(2H, t), 4.13–4.83(2H, m), 7.40(5H, s). |
| 46 | Ph | Ph | 1 | 79 | 241–244 | (CDCl$_3$); 2.06–2.96(3H, m), 3.13–3.47(1H, m), 4.14–4.73(2H, m), 7.15–7.54(10H, m). |
| 47 | Pr | H | 0 | 85 | 120–122 | |
| 48 | Pr | Ph | 0 | 87 | 205–207 | (CDCl$_3$); 0.95(3H, t), 1.46–1.91(2H, m), 2.74–3.15(1H, m), 3.21–3.48(1H, m), 3.94(2H, t), 4.64–4.90(2H, m), 7.36–7.63(5H, m). |
| 49 | Bzl | Ph | 1 | 78 | 201–203 | (CDCl$_3$); 2.22–2.43(1H, m), 2.52–2.65(1H, m), 2.64–2,79(1H, m), 3.25–3.38(1H, m), 4.25–4.40(1H, m), 4.64–4.76(1H, m), 5.20(2H, s), 7.26–7.58(10H, m). |
| 50 | Pen | Ph | 1 | 95 | 158–159 | (CDCl$_3$); 0.90(3H, t), 1.30–1.40(4H, m), 1.61–1.75(2H, m), 2.22–2.44(1H, m), 2.51–2.82(2H, m), 3.25–3.40(1H, m) 4.00(2H, t), 4.33(1H, ddd), 4.26(1H, ddd), 7.34–7.52(5H, m). |
| 51 | Hex | Ph | 1 | 68 | 115–116 | (CDCl$_3$); 0.88(3H, t), 1.25–1.40(6H, m), 1.58–1.72(2H, m), 2.25–2.46(1H, m), 2.50–2.82(2H, m), 3.26–3.41(1H, m), 4.00(2H, t), 4.27–4.41(1H, m), 4.64–4.77(1H, m), 7.35–7.51(5H, m). |
| 52 | Hep | Ph | 1 | 72 | 126–127 | (CDCl$_3$); 0.87(3H, t), 1.21–1.40(8H, m) 1.59–1.72(2H, m), 2.25–2.45(1H, m), 2.53–2.83(2H, m), 3.26–3.40(1H, m), 4.00(2H, t), 4.34(1H, ddd), 4.70(1H, ddd) 7.34–7.50(5H, m). |
| 53 | 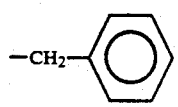 | Ph | 1 | 78 | 201–203 | (DMSO-d$_6$); 2.22–2.43(1H, m), 2.52–2.65(1H, m), 2.64–2.79(1H, m), 3.25–3.38(1H, m), 4.25–4.40(1H, m), 4.64–4.76(1H, m), 5.20(2H, s), 7.26–7.58(10H, m). |
| 54 | 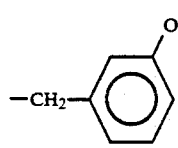 | Ph | 1 | 96 | 158–160 | (CDCl$_3$); 2.19–2.42(1H, m), 2.51–2.68(1H, m), 2.66–2.80(1H, m), 3.23–3.39(1H, m), 3.79(3H, s), 4.32(1H, ddd), 4.70(1H, ddd), 5.17(2H, dd), 6.81–6.87(1H, m), 7.09–7.50(8H, m). |

-continued

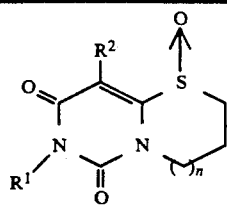

| Example No. | R$^1$ | R$^2$ | n | Yield (%) | m.p. (°C.) | $^1$H-NMR(δ) |
|---|---|---|---|---|---|---|
| 55 | -CH$_2$-C$_6$H$_4$-OMe | Ph | 1 | 87 | 160-162 | (CDCl$_3$); 2.19-2.42(1H, m), 2.50-2.77(2H, m), 3.22-3.37(1H, m) 3.78(3H, s), 4.30(1H, ddd), 4.69(1H, ddd) 5.12(2H, s), 6.83(2H, dt), 7.51(2H, dt), 7.28-7.47(5H, m). |
| 56 | -CH$_2$-C$_6$H$_4$-Cl (ortho) | Ph | 1 | 83 | 228-231 | (CDCl$_3$); 2.22-2.47(1H, m), 2.50-2.83(2H, m), 3.25-3.40(1H, m), 3.34(1H, ddd), 4.70(1H, ddd), 5.15(2H, ddd), 7.24-7.31(1H, m), 7.33-7.62(8H, m). |
| 57 | -CH$_2$-C$_6$H$_4$-Cl | Ph | 1 | 88 | 199-200 | (CDCl$_3$); 2.23-2.48(1H, m), 2.51-2.87 (2H, m), 3.36(1H, ddd), 4.36(1H, ddd), 4.70(1H, ddd), 5.35(2H, s), 7.10-7.23(3H, m), 7.33-7.49(6H, m). |

EXAMPLE 58

1,1-Dioxo-9-phenyl-7-propyl-3,4-dihydro-2H,6H-pyrimido [6,1-b][1,3]thiazine-6,8(7H)-dione m-Chloroperbenzoic acid (0.66 g) was added to a solution of 1-oxo-9-phenyl-7-propyl-3,4-dihydro-2H,6H-pyrimidopyrazole[6,1-b][1,3]thiazine-6,8(7H)-dione (1 g) in methylene chloride (20 ml) little by little with stirring under ice cooling. The reaction mixture was stirred at 5° C. for 1.5 hours, and further stirred at room temperature for 20 hours. The insoluble material was removed by filtration, and the filtrate was washed with a saturated aqueous sodium bicarbonate. After drying, the organic layer was concentrated to dryness. The resulting crude crystals were recrystallized from methylene chloride-hexane to give colorless needles (0.77 g, 73%).

Melting point: 179°-180° C.

| Elemental analysis for C$_{16}$H$_{18}$N$_2$O$_4$S: | | | |
|---|---|---|---|
| | C (%) | H (%) | N (%) |
| Calcd: | 57.47; | 5.43; | 8.38 |
| Found: | 57.07; | 5.42; | 8.75 |

$^1$H-NMR(CDCl$_3$)δ: 0.93(3H,t),1.45-1.91(2H,m), 2.26-2.62(2H,m),3.30(2H,t),3.93(2H,t), 4.24(2H,t),7.21-7.51(5H,m)

EXAMPLES 59 TO 67

The following compounds were synthesized by methods similar to that of Example 58.

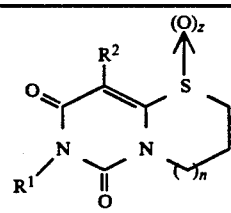

| Example No. | R$^1$ | R$^2$ | n | Yield (%) | m.p. (°C.) | $^1$H-NMR(δ) |
|---|---|---|---|---|---|---|
| 59 | Me | Ph | 0 | 70 | 188-189 | (CDCl$_3$); 3.43(3H, s), 3.43(2H, t), 4.30(2H, t), 7.49(5H, s). |
| 60 | Et | Ph | 0 | 68 | 210-211 | (CDCl$_3$); 1.26(3H, t), 3.41(2H, t), 4.05(2H, q)4.28(2H, t), 7.43(5H, s). |
| 61 | Pr | Ph | 0 | 72 | 157-158 | (CDCl$_3$); 0.95(3H, t), 1.45-1.91(2H, m), 3.42(2H, t), 3.94(2H, t), 4.29(2H, t), 7.48(5H, s). |
| 62 | Bu | Ph | 0 | 87 | 160-161 | (CDCl$_3$); 0.94(3H, t), 1.05-1.81(4H, m), 3.42(2H, t), 3.99(2H, t), 4.29(2H, t), 7.48(5H, s). |
| 63 | Ph | Ph | 0 | 56 | 247-249 | (CDCl$_3$); 3.38(2H, t), |

-continued

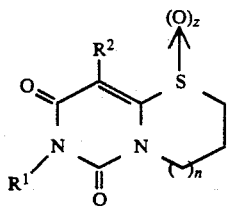

| Example No. | R¹ | R² | n | Yield (%) | m.p. (°C.) | ¹H-NMR(δ) |
|---|---|---|---|---|---|---|
| 64 | Me | Ph | 1 | 33 | 188–189 | 4.24(2H, t), 7.14–7.65(10H, m). (CDCl₃); 2.26–2.62(2H, m), 3.31(2H, t), 3.41(3H, s), 4.26(2H, t), 7.19–7.52(5H, m). |
| 65 | Et | Ph | 1 | 71 | 206–208 | (CDCl₃); 1.25(3H, t), 2.23–2.55(2H, m), 3.29(2H, t), 4.22(2H, t), 4.02(2H, q), 7.22–7.53(5H, m). |
| 66 | Bu | Ph | 1 | 77 | 173–174 | (CDCl₃); 0.93(3H, t), 1.04–1.84(4H, m), 2.24–2.60(2H, m), 3.31(2H, t), 3.97(2H, t), 4.25(2H, t), 7.19–7.51(5H, m). |
| 67 | Ph | Ph | 1 | 77 | 277–279 | (CDCl₃); 2.29–2.62(2H, m), 3.35(2H, t), 4.29(2H, t), 7.13–7.56(10H, m). |

EXAMPLE 68

9-Phenyl-3,4-dihydro-2H,6H-pyrimido[6,1-b][1,3]thiazine-6,8(7H)-dione

Boron trifluoride (0.68 ml) was added to a solution of 7-benzyl-9-phenyl-3,4-dihydro-2H,6H-pyrimido[6,1-b][1,3]thiazine-6,8(7H)-dione (1 g) in toluene (40 ml) and was refluxed for 14 hours. Methanol (7 ml) was added to the reaction solution and the mixture was stirred for 30 minutes. The resulting solution was concentrated to dryness, and the residue was dissolved in methylene chloride and ethyl ether. The insoluble material was obtained by filtration and the product was washed by aqueous methanol. After the washing, it was recrystallized from DMF-water to give colorless crystals (0.33 g, 44%).
Melting point: >300° C.

| Elemental analysis for $C_{13}H_{12}N_2O_2S$: | | | |
|---|---|---|---|
| | C (%) | H (%) | N (%) |
| Calcd: | 59.98; | 4.65; | 10.76 |
| Found: | 59.90; | 4.65; | 10.79 |

¹H-NMR(200MHz, DMSO-d₆)δ: 2.04–2.16(2H,m),2.99(2H,t), 3.89(2H,t),7.14–7.21(2H,m), 7.29–7.42(3H,m), 11.37(1H, brs)

EXAMPLES 69

7-Pentyl-9-phenyl-3,4-dihydro-2H,6H-pyrimido[6,1-b][1,3]thiazine-6,8(7H)-dione

1-Iodopentane (2.29 g), potassium carbonate (1.28 g) and 9-phenyl-3,4-dihydro-2H,6H-pyrimido[6,1-b][1,3]thiazine-6,8(7H)-dione (2 g) in DMF (30 ml) were stirred at 100° C. for 15 hours. The reaction solution was concentrated to dryness, and the residue was purified by column chromatography on silica gel. The obtained crude crystals were recrystalized from ethyl acetate-hexane to give colorless crystals (1.64 g, 65%).
Melting point: 100°–101° C.

| Elemental analysis for $C_{18}H_{22}N_2O_2S$ | | | |
|---|---|---|---|
| | C (%) | H (%) | N (%) |
| Calcd: | 65.43; | 6.71; | 8.48 |
| Found: | 65.69; | 6.80; | 8.44 |

¹H-NMR(200MHz, CDCl₃)δ: 0.89(3H,t),1.26–1.42(4H,m), 1.60–1.73(2H,m),2.19–2.31(2H,m),2.96(2H,t), 3.97(2H,t),4.11(2H,t), 7.23–7.29(2H,m), 7.35–7.46(3H,m).

EXAMPLES 70 TO 77

The following compounds were synthesized by methods similar to that of Example 69.

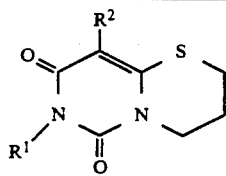

| Example No. | R¹ | R² | Yield (%) | m.p. (°C.) | ¹H-NMR(200MHz, CDCl₃)δ |
|---|---|---|---|---|---|
| 70 | −CH₂−（Cl-phenyl, ortho） | Ph | 85 | 191–192 | 2.19–2.31(2H, m), 2.98(2H, t), 4.11(2H, t), 5.31(2H, s), 7.11–7.47(9H, m). |
| 71 | −CH₂−（4-OMe-phenyl） | Ph | 87 | 188–190 | 2.15–2.28(2H, m), 2.93(2H, t), 4.08(2H, t), 3.78(3H, s), 5.10(2H, s), 6.83(2H, d), 7.53(2H, d), 7.21–7.28(2H, m), 7.36–7.48(3H, m). |
| 72 | −CH₂−（2-OMe-phenyl） | Ph | 92 | Oily product | 2.15–2.28(2H, m), 2.92(2H, t), 4.07(2H, t), 3.78(3H, s), 5.14(2H, s), 6.78–6.83(1H, m), 7.07–7.47(8H, m). |
| 73 | −CH₂−（3-Cl-phenyl） | Ph | 100 | Oily product | 2.16–2.29(2H, m), 2.94(2H, t), 4.08(2H, t), 5.12(2H, s), 7.20–7.53(9H, m), |
| 74 | −CH₂−（4-Cl-phenyl） | Ph | 80 | 196–197 | 2.16–2.29(2H, m), 2.95(2H, t), 4.09(2H, t), 5.12(2H, s). 7.22–7.31(4H, m), 7.35–7.54(5H, m). |
| 75 | −CH₂−（2-F-phenyl） | Ph | 80 | 151–152 | 2.18–2.30(2H, m), 2.96(2H, t), 4.10(2H, t), 5.27(2H, s), 6.99–7.10(2H, m), 7.18–7.48(7H, m). |
| 76 | Hex | Ph | 65 | 77–78 | 0.87(3H, t), 1.25–1.44(6H, m), 1.59–1.75(2H, m), 2.18–2.30(2H, m), 2.95(2H, t), 3.97(2H, t), 4.10(2H, t), 7.23–7.30(2H, m), 7.34–7.46(3H, m). |
| 77 | Hep | Ph | 73 | Oily product | 0.87(3H, t), 1.22–1.41(8H, m), 1.59–1.74(2H, m), 2.18–2.30(2H, m), 2.95(2H, t), 3.97(2H, t), 4.11(2H, t), 7.23–7.29(2H, m), 7.35–7.47(3H, m). |

EXAMPLES 78

2-Hydroxy-9-phenyl-7-propyl-3,4-dihydro-2H,6H-pyrimido[6,1-b][1,3]thiazine-6,8(7H)-dione Trifluoroacetic anhydride (3.78 g) and triethylamine (1.82 g) were added to a solution of 1-oxo-9-phenyl-7-propyl-3,4-dihydro-2H,6H-pyrimido[6,1-b][1,3]thiazine-6,8(7H)-dione (4 g) in methylene chloride (60 ml) and the mixture was stirred at 40° C. for 60 hours. The reaction solution was evaporated to dryness, and the residue was dissolved in methylene chloride-H₂O. Then, the organic layer was washed with a saturated aqueous sodium bicarbonate. After drying, the organic solution was concentrated, and the resulting residue was purified by column chromatography on silica gel. The resulting crude crystals were recrystalized from methylene chloride-isopropyl ether to give colorless needles (3.1 g, 78%).

Melting point: 170°–171° C.

| Elemental analysis for C₁₆H₁₈N₂O₃S | | | |
|---|---|---|---|
| | C (%) | H (%) | N (%) |
| Calcd: | 60.36; | 5.70; | 8.80 |
| Found: | 60.03; | 5.68; | 8.58 |

¹H-NMR(CDCl₃)δ: 0.89(3H t).1 41–1.87(2H m) 2.23–2.99(2H,q),3.88(2H,t), 3.97–4.39(2H,m),4.52(1H,d),5.07(1H,q), 7.07–7.43(5H,m).

EXAMPLE 79 TO 82

The following compounds were synthesized by methods similar to that of Example 78.

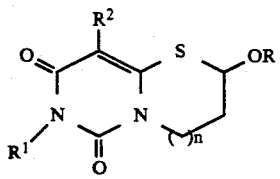

| Example No. | $R^1$ | $R^2$ | R | n | Yield (%) | m.p. (°C.) | $^1$H-NMR (δ) |
|---|---|---|---|---|---|---|---|
| 79 | Pr | H | H | 0 | 45 | 168–169 | (d$_6$-DMSO); 0.86(3H, t), 1.31–1.77(2H, m), 3.72(2H, t), 4.15–4.33(2H, m), 5.72(1H, s), 5.87(1H, brs), 7.27(1H, d). |
| 80 | Pr | H | Ac | 0 | 75 | Syrup | (CDCl$_3$); 0.93(3H, t), 1.43–1.87(2H, m), 2.11(3H, s), 3.84(2H, t), 4.25(1H, q), 4.71(1H, d), 5.69(1H, s), 6.26(1H, d). |
| 81 | Bu | Ph | H | 1 | 85 | 170–172 | (CDCl$_3$); 0.92(3H, t), 1.27–1.45(2H, m), 1.56–1.71(2H, m), 2.21–2.31(2H, m), 3.46(1H, brs), 3.96(2H, t), 4.00–4.15(1H, m), 4.21–4.33(1H, m), 5.24(1H, q), 7.18–7.43(5H, m). |
| 82 | Bzl | Ph | H | 1 | 53 | 238–241 | (d$_6$-DMSO); 2.03–2.18(1H, m), 2.27–2.42(1H, m), 4.06(2H, t), 5.03(2H, s), 5.45(1H, q), 6.96(1H, d), 7.17–7.44(10H, m). |

EXAMPLE 83

1-Oxo-9-phenyl-7-propyl-2H,6H-pyrimido[6,1-b][1,3]thiazine-6,8(7H)-dione m-Chloroperbenzoic acid (0.34 g) was added to a solution of 9-phenyl-7-propyl-4H,6H-pyrimido[6,1-b][1,3]thiazine-6,8(7H)-dione (0.53 g) in methylene chloride (10 mll) little by little with stirring under ice cooling, and then, the reaction mixture was stirred at room temperature for 10 hours. An insoluble material was removed by filtration, and the filtrate was washed with a saturated aqueous sodium bicarbonate. After drying, the organic solution was concentrated to dryness. The resulting residue was purified column chromatography on silica gel. The resulting crude crystals were recrystalized from methylene chloride-isopropyl ether to give colorless needles (0.47 g, 87%).

Melting point: 174°–175° C.

| Elemental analysis for $C_{16}H_{16}N_2O_3S$ | | | |
|---|---|---|---|
| | C (%) | H (%) | N (%) |
| Calcd: | 60.74; | 5.10; | 8.85 |
| Found: | 60.76; | 5.07; | 8.60 |

$^1$H-NMR(CDCl$_3$)δ: 0.96(3H,t),1.48–1.94(2H,m), 3.28(1H,se),3.81(1H,q),3.99(2H,t) 5.53(1H,se),7.4(5H,m),7.68(1H,q)

EXAMPLE 84

9-Phenyl-2-phenylthio-7-propyl-3,4-dihydro-2H,6H-pyrimido[6,1-b][1,3]thiazine-6,8(7H)-dione Boron trifluoride ethyl etherate (0.2 ml) was added to a solution of 2-hydroxy-7-phenyl-7-propyl-3,4-dihydro-2H,6H-pyrimido[6,1-b][1,3]thiazine-6,8(7H)-dione (0.6 g) and thiophenol (0.23 g) in methylene chloride (10 ml) and the mixture was stirred at room temperature for 70 hours. The reaction solution was evaporated to dryness, and the residue was dissolved in methylene chloride. The solution was washed with 1N aqueous sodium hydroxide and water, followed by drying. The solvent was evaporated and the resulting syrup was crystallized from ethyl acetate-hexane to give colorless crystals (0.68 g, 85%).

Melting point: 126°–127° C.

| Elemental analysis for $C_{22}H_{22}N_2O_2S$ | | | |
|---|---|---|---|
| | C (%) | H (%) | N (%) |
| Calcd: | 64.36; | 5.40; | 6.82 |
| Found: | 64.17; | 5.39; | 6.77 |

$^1$H-NMR(CDCl$_3$)δ: 0.93(3H,t),1.87–2.71(2H,m), 3.93(2H,t),3.79–4.68(3H,m) 7.14–7.52(10H,m)

EXAMPLE 85

2-Ethoxy-9-phenyl-7-propyl-3,4-dihydro-2H,6H-pyrimido[6,1-b][1,3]thiazine-6,8(7H)-dione A 2-ethoxy derivative (syrup, 92%) was obtained by a method similar to that of Example 69.

$^1$H-NMR(CDCl$_3$)δ: 0.93(3H,t).1.46–1.91(2H,m). 3.12–3 78(2H,m),3.93(2H,t), 3.85–4.47(2H,m),4.96(1H,t) 7.16–7.45(5H,m).

EXAMPLE 86

8-Nitro-6-propyl-2,3-dihydro-5H-thiazolo[3,2-c]pyrimidine-5,7(6H)-dione

6-Propyl-2,3-dihydro-5H-thiazolo[3,2-c]pyrimidine-5,7-(6H)-dione (2.12 g) was added to concentrated sulfuric acid (5.2 ml) little by little under ice cooling, and then, fuming nitric acid (1.8 ml) was added dropwise thereto with stirring. The mixture was stirred under ice cooling for 1 hour. The reaction temperature was kept under 5° C. for this period. The reaction solution was poured on ice water, and the resulting crystals were collected by filtration and recrystallization from ethanol-ethyl acetate to give pale yellow needles (2.0 g, 85%).

Melting point: 189°–191° C.

| Elemental analysis for C₉H₁₁N₃O₄S | | | |
|---|---|---|---|
| | C (%) | H (%) | N (%) |
| Calcd: | 42.02; | 4.31; | 16.33 |
| Found: | 41.97; | 4.34; | 16.22 |

¹H-NMR(CDCl₃)δ: 0.93(3H,t),1.43–1.90(2H,m), 3.40(2H,t),3.88(2H,t),4.57(2H,t)

EXAMPLE 87

9-Acetylamino-7-propyl-3,4-dihydro-2H,6H-pyrimido[6,1-b][1,3]thiazine-6,8(7H)-dione Zinc powder (1,21 g) was added to a solution of 9-nitro-7-propyl-3,4-dihydro-2H,6H-pyrimido[6,1-b][1,3]thiazine-6,8(7H)-dione (1 g) in acetic acid (10 ml) and the mixture was refluxed for 4 hours. An insoluble material was removed by filtration, and the filtrate was concentrated to obtain syrup. The syrup was purified by column chromatography on silica gel. The resulting crude crystals were recrystallized from methylene chloride-hexane to give colorless needles (0.83 g, 79%).

Melting point: 172–°174° C.

| Elemental analysis for C₁₂H₁₇N₃O₃S | | | |
|---|---|---|---|
| | C (%) | H (%) | N (%) |
| Calcd: | 50.87; | 6.05; | 14.83 |
| Found: | 50.85; | 6.04; | 14.84 |

¹H-NMR(CDCl₃)δ: 0.92(3H,t),2.15(3H,s),3.01(2H,t), 3.88(2H,t),4.03(2H,t),7.35(1H,brs)

EXAMPLES 88 TO 91

The following compounds were synthesized by methods similar to that of Example 87.

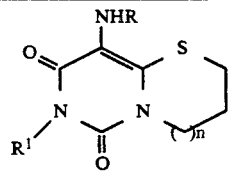

| Example No. | R¹ | R | n | Yield (%) | m.p. (°C.) | ¹H-NMR (δ) |
|---|---|---|---|---|---|---|
| 88 | Pr | CHO | 0 | 50 | 156–160 | (d₆-DMSO); 0.86(3H, t), 1.33–1.79(2H, m), 3.40(2H, t), 3.75(2H, t), 4.32(2H, t), 8.11(1H, s), 9.30(1H, brs). |
| 89 | Pr | CHO | 1 | 75 | 166–167 | (CDCl₃); 0.91(3H, t), 1.42–1.87(2H, m), 2.09–2.43(2H, m), 3.04(2H, t), 3.89(2H, t), 4.04(2H, t), 7.67(1H, brs), 8.28(1H, s). |
| 90 | Pr | Ac | 0 | 50 | 203–205 | (CDCl₃); 0.91(3H, t), 1.39–1.85(2H, m), 2.13(3H, s), 3.29(2H, t), 3.85(2H, t), 4.39(2H, t), 7.66(1H, brs). |
| 91 | Pr | CHO | 2 | 77 | 162–163 | (CDCl₃); 0.93(3H, t), 1.24–2.18(6H, m), 2.94(2H, t), 3.91(2H, t), 4.41(2H, t), 7.82(1H, brs), 8.31(1H, s). |

EXAMPLE 92

9-Amino-7-propyl-3,4-dihydro-2H,6H-pyrimido[6,1-b][1,3]-thiazone-6,8(7H)-dione

1N Aqueous hydrochloric acid (10 ml) was added to a solution of 9-formylamino-7-propyl-3,4-dihydro-2H,6H-pyrimido[6,1-b][1,3]thiazine-6,8(7H)-dione (2 g) in methanol (30 ml), and the solution was refluxed for 3 hours. The reaction solution was concentrated to dryness, and the resulting residue was dissolved in water. The solution was neutralized with 1N aqueous sodium hydroxide, and allowed to cool to give colorless needles (1.55 g, 87%).

Melting point: 124°–125° C.

| Elemental analysis for C₁₀H₁₅N₃O₂S | | | |
|---|---|---|---|
| | C (%) | H (%) | N (%) |
| Calcd: | 49.77; | 6.27; | 17.41 |
| Found: | 49.79; | 6.26; | 17.44 |

¹H-NMR(CDCl₃)δ: 0.92(3H,t),3.37(2H,brs),3.09(2H,t), 3.91(2H,t),4.02(2H,t)

EXAMPLE 93

8-Amino-6-propyl-2,3-dihydro-5H-thiazolo[3,2-c]-pyrimidine-5,7(6H)-dione

An 8-amino derivative was obtained by a method similar to that of Example 92 in a 56% yield.

Melting point: 120°–122° C.

| Elemental analysis for C₉H₁₃N₃O₂S | | | |
|---|---|---|---|
| | C (%) | H (%) | N (%) |
| Calcd: | 47.56; | 5.77; | 18.49 |
| Found: | 47.46; | 5.78; | 18.48 |

¹H-NMR(CDCl₃)δ: 0.93(3H,t),1.41–1.88:(2H,m), 3.11(2H,brs),3.35(2H,t),3.88(2H,t) 4.33(2H,t)

EXAMPLE 94

9-Butyrylamino-7-propyl-3,4-dihydro-2H,6H-pyrimido[6,1-b][1,3]thiazine-6,8(7H)-dione Butyric anhydride (1.32 g) and 4-dimethylaminopyridine (20 mg) were added to a solution of 9-amino-7-propyl-3,4-dihydro-2H,6H-pyrimido[6,1-b][1,3]thiazine-6,8(7H)-dione (1 g) in pyridine (20 ml) and the solution was heated at 50° C. for 4 hours. The reaction solution was concentrated to dryness, and the residue was dissolved in methylene chloride-water. The organic solution was washed with water, dried and concentrated to dryness. The resulting crude crystals were recrystallized from ethanol-ether to give colorless crystals (0.93 g, 72%).

Melting point: 171°–172° C.

| | Elemental analysis for $C_{14}H_{21}N_3O_3S$ | | |
|---|---|---|---|
| | C (%) | H (%) | N (%) |
| Calcd: | 54.00; | 6.80; | 13.49 |
| Found: | 53.98; | 6.81; | 13.54 |

$^1$H-NMR(CDCl$_3$)δ:
0.91(3H,t),1.00(3H,t),1.41–1.97(4H,m),
2.06–2.46(4H,m),3.00(2H,t),3.88(2H,t),
4.04(2H,t),7.16(1H,brs).

EXAMPLES 95 TO 100

The following compounds were synthesized by methods similar to that of Example 94.

EXAMPLE 101

9-Formyl-7-propyl-3,4-dihydro-2H,6H-pyrimido[6,1-b][1,3]thiazine-6,8(7H)-dione The Vilsmeier reagent prepared from phosphorus oxychloride (3.7 ml) and DMF (6.2 ml) was added dropwise to a solution of 7-propyl-3,4-dihydro-2H,6H-pyrimido[6,1-b][1,3]thiazine-6,8(7H)-dione (6 g) in DMF (38 ml) with stirring under ice cooling. The reaction solution was stirred at room temperature for 3 hours and then, poured on ice water. The mixture was stirred for a while and the precipitated crystals were recrystallized from ethyl acetate to give colorless crystals (6.46 g, 95%).

Melting point: 153°–154° C.

| | Elemental analysis for $C_{10}H_{12}N_2O_3S$ | | |
|---|---|---|---|
| | C (%) | H (%) | N (%) |
| Calcd: | 49.99; | 5.03; | 11.66 |
| Found: | 49.23; | 5.05; | 11.56 |

$^1$H-NMR(CDCl$_3$)δ:
0.94(3H,t),1.45–1.89(2H,m),3.35(2H,t),
3.89(2H,t),4.39(2H,t),10.08(1H,s)

EXAMPLE 102

8-Formyl-6-propyl-2,3-dihydro-5H-thiazolo[3,2-c]pyrimidine-5,7(6H)-dione

An 8-formyl derivative was synthesized by a method similar to that of Example 101 in a 62% yield.

Melting point: 153°–154° C.

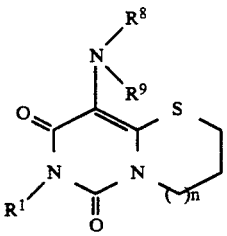

| Example No. | $R^1$ | $R^8$ | $R^9$ | n | Yield (%) | m.p. (°C.) | $^1$H-NMR (δ) |
|---|---|---|---|---|---|---|---|
| 95 | Pr | Me | Me | 0 | 80 | 122–150 (Hydrochloride) | (CDCl$_3$); 0.91(3H, t), 1.41–1.85(2H, m), 2.68(6H, s), 3.27(2H, t), 3.81(2H, t), 4.35(2H, t). |
| 96 | Pr | H | Bu | 0 | 40 | 143–145 (Hydrochloride) | (CDCl$_3$); 0.92(6H, t), 1.13–1.87(6H, m), 2.89(2H, t), 3.31(2H, t), 3.87(2H, t), 4.32(2H, t). |
| 97 | Pr | Bu | Bu | 0 | 42 | Syrup | (CDCl$_3$); 0.88(3H, t), 0.92(3H, t), 0.94(3H, t), 1.07–1.80(10H, m), 2.94(4H, t), 3.23(2H, t), 3.82(2H, t), 4.36(2H, t). |
| 98 | Pr | H | COPr | 0 | 73 | 182–183 | (CDCl$_3$); 0.93(3H, t), 1.00(3H, t), 1.38–1.95(4H, m), 2.34(2H, t), 3.27(2H, t), 3.86(2H, t), 4.39(2H, t), 7.43(1H, brs). |
| 99 | Pr | Me | Me | 1 | 45 | 90–113 (Hydrochloride) | (CDCl$_3$); 0.92(3H, t), 1.40–1.88(2H, m), 2.03–2.35(2H, m), 2.67(6H, s), 2.93(2H, t), 3.85(2H, t), 3.90(2H, t). |
| 100 | Pr | H | Bu | 1 | 41 | Syrup | (CDCl$_3$); 0.92(6H, t), 1.16–1.88(6H, m), 2.05–2.38(2H, m), 2.83(2H, t), 3.03(2H, t), 3.93(2H, t), 3.99(2H, t). |

| Elemental analysis for $C_{10}H_{12}N_2O_3S$ | | | |
|---|---|---|---|
| | C(%) | H(%) | N(%) |
| Calcd: | 49.99 | 5.03 | 11.66 |
| Found: | 49.23 | 5.05 | 11.56 |

$^1$H-NMR(CDCl$_3$)δ:
0.94(3H,t),1.45–1.89(2H,m),3.35(2H,t),
3.89(2H,t),4.39(2H,t),10.08(1H,s)

EXAMPLE 103

2-Cyano-3-(5,7-dioxo-6-propyl-2,3,6,7-tetrahydro-5H-thiazolo[3,2-c]pyrimidine-8-yl)acrylonitrile A solution of 8-formyl-6-propyl-2,3-dihydro-5H-thiazolo[3,2-c]pyrimidine-5,7(6H)-dione(1 g), malononitrile (0.31 g) and ethanol (20 ml) containing 10% aqueous solution of potassium hydroxide (0.1 ml), were stirred at 60° C. for 7 hours. The reaction solution was concentrated under reduced pressure, and the residue was dissolved in chloroform. After washing with water and drying, the organic solution was concentrated to dryness. The resulting residue was purified by column chromatography on silica gel. The resulting crude crystals were recrystallized from ethyl acetate-isopropyl ether to give pale yellow-red needles (0.23 g, 19%).

Melting point: 135°–137° C.

| Elemental analysis for $C_{13}H_{12}N_4O_2S$ | | | |
|---|---|---|---|
| | C(%) | H(%) | N(%) |
| Calcd: | 54.15 | 4.19 | 19.43 |
| Found: | 53.94 | 4.02 | 19.72 |

$^1$H-NMR(CDCl$_3$)δ: 0.92(3H,t),1.49–1.85(2H,m)
3.52(2H,t),3.86(2H,t),4.52(2H,t),
7.31(1H,s)

EXAMPLE 104

Ethyl(E)-3-(5,7-dioxo-6-propyl-2,3,6,7-tetrahydro-5H-thiazolo[3,2-c]pyrimidine-8-yl)acrylate A solution of the Wittig reagent prepared from triphenylphosphine (5.3 g) and ethyl bromoacetate (3.4 g), (carboethoxymethylene)triphenylphosphorane (6 g) and 8-formyl-6-propyl-2,3-dihydro-5H-thiazolo[3,2-c]pyrimidine-5,7(6H)-dione (3.76 g) in methylene chloride (15 ml) was refluxed in for 7 hours. The reaction solution was concentrated to dryness. The resulting residue was purified by column chromatography on silica gel. The resulting crude crystals were recrystallized from methylene chloride -isopropyl ether to give colorless needles (3.82 g, 79%).

Melting point: 140°–141° C.

| Elemental analysis for $C_{14}H_{18}N_2O_4S$ | | | |
|---|---|---|---|
| | C(%) | H(%) | N(%) |
| Calcd: | 54.18 | 5.85 | 9.03 |
| Found: | 54.15 | 5.81 | 8.95 |

EXAMPLES 105 TO 112

The following compounds were synthesized by methods similar to that of Example 104.

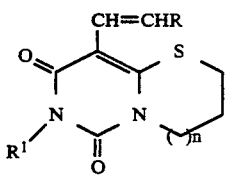

| Example No. | R$^1$ | R | n | Yield (%) | m.p. (°C.) | $^1$H-NMR (δ) |
|---|---|---|---|---|---|---|
| 105 | Pr | (Z)-CN | 0 | 54 | 165–167 | (CDCl$_3$); 0.93(3H, t), 1.42–1.89(2H, m), 3.40(2H, t), 3.87(2H, t), 4.10(2H, t), 5.49(1H, d), 6.96(1H, d). |
| 106 | Pr | (E)-Bu | 0 | 65 | 63–68 | (CDCl$_3$); 0.90(3H, t), 0.93(3H, t), 1.10–1.97(6H, m), 2.19(2H, q), 3.31(2H, t), 3.88(2H, t), 4.35(2H, t), 6.08(1H, d), 6.35(1H, dt). |
| 107 | Pr | (E)-Ph | 0 | 15 | 168–170 | (CDCl$_3$); 0.95(3H, t), 1.42–1.92(2H, m), 3.32(2H, t), 3.89(2H, t), 4.36(2H, t), 6.76(1H, d), 7.13–7.56(6H, m). |
| 108 | Pr | (Z)-CN | 1 | 43 | 143–144 | (CDCl$_3$); 0.93(3H, t), 1.43–1.87(2H, m), 2.09–2.41(2H, m), 3.12(2H, t), 3.91(2H, t), 4.08(2H, t), 5.56(1H, d), 6.84(1H, d). |
| 109 | Pr | (E)-CN | 1 | 28 | 154–155 | (CDCl$_3$); 0.93(3H, t), 1.41–1.87(2H, m), 2.10–2.43(2H, m), 3.16(2H, t), 3.88(2H, t), 4.11(2H, t), 6.79(1H, d), 7.34(1H, d). |
| 110 | Pr | (E)-COOEt | 1 | 89 | 128–129 | (CDCl$_3$); 0.92(3H, t), 1.26(3H, t), 1.40–1.85(2H, m), 2.06–2.39(2H, m), 3.12(2H, t), 3.89(2H, t), 4.10(2H, q), |

-continued

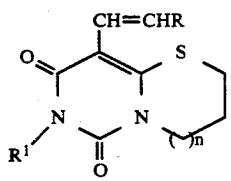

| Example No. | R[1] | R | n | Yield (%) | m.p. (°C.) | 1H-NMR (δ) |
|---|---|---|---|---|---|---|
| 111 | Pr | (E)-Bu | 1 | 18 | 58–60 | 4.18(2H, t), 7.10(1H, d), 7.72(1H, d). (CDCl$_3$); 0.88(3H, t), 0.91(3H, t), 1.06–1.99(6H, m), 2.01–2.35(4H, m), 3.03(2H, t), 3.89(2H, t), 4.05(2H, t), 6.11(1H, d), 6.55(1H, dt). |
| 112 | Pr | (E)-Ph | 1 | 49 | 159–160 | (CDCl$_3$); 0.98(3H, t), 1.60–1.79(2H, m), 2.20–2.34(2H, M), 3.14(2H, t), 3.97(2H, t), 4.14(2H, t), 7.00(1H, d), 7.19–7.51(5H, m), 7.74(1H, d). |

EXAMPLE 113

9-Dimethylammoniomethyl-7-propyl-3,4-dihydro-2H,6H-pyrimido[6,1-b][1,3]thiazine-6,8(7H)-dione chloride A mixture of 7-propyl-3,4-dihydro-2H,5H-pyrimido[6,1-b][1,3]thiazine-6,8(7H)-dione (1 g), paraformaldehyde (0.22 g) and dimethylamine hydrochloride (0.51 g) in acetic acid (25 ml) was refluxed for 18 hours. The reaction solution was concentrated dryness, and the resulting residue was dissolved in water. Then, the solution was made basic with 1N aquaous sodium hydroxide, followed by extraction of the product with methylene chloride. After washing with water and drying, the organic layer was concentrated to dryness to obtain a syrup. The syrup was converted to the hydrochloride to form crystals, which were recrystallized from ethanol-ethyl acetate to give colorless prisms (0.46 g, 33%).

Melting point: 201°–203° C.

| Elemental analysis for C$_{13}$H$_{21}$N$_3$O$_2$S.HCl | | | |
|---|---|---|---|
| | C(%) | H(%) | N(%) |
| Calcd: | 48.82 | 6.93 | 13.14 |
| Found: | 48.77 | 7.19 | 13.09 |

1H-NMR(CDCl$_3$)δ: 0.92(3H,t),1.40–1.87(2H,m), 2.03–2.38(2H,m),2.25(6H,s),3.03(2H,t), 3.33(2H,s), 3.89(2H,t),4.04(2H,t)

EXAMPLES 114 TO 116

The following compounds were synthesized by methods similar to that of Example 113.

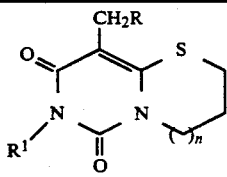

| Example No. | R[1] | R | n | Yield (%) | m.p. (°C.) | 1H-NMR (δ) |
|---|---|---|---|---|---|---|
| 114 | Pr | —N(Me)(Me) | 0 | 62 | 102–104 | (CDCl$_3$); 0.92(3H, t), 1.42–1.87(2H, m), 2.21(6H, s), 3.21(2H, s), 3.21(2H, t), 3.86(2H, t), 4.30(2H, t). |
| 115 | Pr | —N(piperidinyl) | 0 | 34 | 241–246 | (CDCl$_3$); 0.91(3H, t), 1.23–1.84(8H, m), 2.36(4H, t), 3.14(2H, t), 3.24(2H, s), 3.83(2H, t), 4.25(2H, t). |
| 116 | Pr | —N(piperidinyl) | 1 | 48 | 203–210 | |

EXAMPLE 117

9-Hydroxymethyl-7-propyl-3,4-dihydro-2H,5H-pyrimido[6,1-b][1,3]thiazine-6,8(7H)-dione Sodium borohydride (0.15 g) was added to a solution of 9-formyl-7-propyl-3,4-dihydro-2H,5H-pyrimido[6,1- b]]1,3]thiazine-6,8(7H)-dione (1 g) in methanol (20 ml), followed by stirring at room temperature for 1 hour. The reaction solution was concentrated to dryness, and the residue was dissolved in water. Then, the solution was made acidic with 1N aqueous hydrochloric acid and extracted with methylene chloride. After washing with water and drying, the organic layer was concentrated to dryness. The resulting residue was purified by column chromatography on silica gel. The resulting crude crystals were recrystallized from ethyl acetate-isopropyl ether colorless needles needles (0.43 g, 43%).

Melting point: 134°-137° C.

| Elemental analysis for $C_{11}H_{16}N_2O_3S$ | | | |
| --- | --- | --- | --- |
|  | C(%) | H(%) | N(%) |
| Calcd: | 51.54 | 6.29 | 10.93 |
| Found: | 51.52 | 6.32 | 10.83 |

$^1$H-NMR(CDCl$_3$)δ: 0.93(3H,t),1.42-1.88(2H,m), 2.06-2.40(2H,m),3.09(2H,t),3.14(1H,t), 3.99(2H,t), 4.06(2H,t),4.56(2H,d)

EXAMPLE 118

8-Hydroxymethyl-6-propyl-2,3-dihydro-5H-thiazolo[3,2-c]pyrimidine-5,7(6H)-dione

The compound was synthesized by a method similar to that of Example 117.

Melting point: 141°-143° C.

| Elemental analysis for $C_{10}H_{14}N_2O_3S$: | | | |
| --- | --- | --- | --- |
|  | C(%) | H(%) | N(%) |
| Calcd: | 49.57 | 5.82 | 11.56 |
| Found: | 49.86 | 5.68 | 11.78 |

$^1$H-NMR(CDCl$_3$)δ:
0.94(3H,t),1.43-1.88(2H,m),2.89(1H,t), 3.34(2H,t),3.86(2H,t),4.36(2H,t) 4.40(2H,d).

EXAMPLE 119

8-[(E)-3-Oxo-3-(L-piperidinyl)propene-1-yl]-6-propyl2,3-dihydro-5H-thiazolo[3,2-c]pyrimidine-5,7(6H)-dione A solution of 2M trimethylaluminum in hexane (5.3 ml) was added to a solution of piperidine (0.69 g) in methylene chloride (25 ml), followed by stirring at room temperature for 15 minutes. Then, a solution of ethyl(E)-3-(5,7-dioxo-6-propyl-2,3,6,7-tetrahydro-5H-thiazolo[3,2-c]pyrimidine-8-yl) acrylate (1 g) in methylene chloride (25 ml) was added thereto, followed by heating under reflux for 16 hours. Hydrochloric acid was added to the reaction solution to decompose the unreacted reagents, and then the organic layer was washed with water and dried. The solution was concentrated dryness, and the resulting residue was purified by column chromatography on silica gel. The resulting crude crystals were recrystalized from methylene chloride-isopropyl ether to give colorless needles (1.03 g, 91%).

Melting point: 237°-238° C.

| Elemental analysis for $C_{17}H_{23}N_3O_3S$ | | | |
| --- | --- | --- | --- |
|  | C(%) | H(%) | N(%) |
| Calcd: | 58.43 | 6.63 | 12.02 |
| Found: | 58.07 | 6.55 | 11.83 |

$^1$H-NMR(CDCl$_3$)δ: 0.94(3H,t),1.45-1.99,:(8H,m), 3.39(2H,t),3.60(4H,brs),3.89(2H,t) 4.42(2H,t),7.19(1H,d),7.67(1H,d)

EXAMPLE 120

9-[(E)-3-Oxo-3-(N-piperidinyl)propene-1-yl]-3,4-dihydro-2H,6H-pyrimido[6,1-b][1,3]thiazine-6,8(7H)-dione The piperidino derivative was synthesized by a method similar to that of Example 104 in 31% yield.

Melting point: 181°-182° C.

| Elemental analysis for $C_{18}H_{25}N_3O_3S$ | | | |
| --- | --- | --- | --- |
|  | C(%) | H(%) | N(%) |
| Calculated: | 59.48 | 6.93 | 11.56 |
| Found: | 59.20 | 6.92 | 11.39 |

$^1$H-NMR(CDCl$_3$)δ: 0.97(3H,t),1.52-1.78(8H,m), 2.20-2.32(2H,m),3.14(2H,t), 3.54-3.70(4H,m),3.94(2H,t),4.14(2H,t), 7.76(2H,s).

EXAMPLE 121

2-Chloromethyl-6-propyl-2,3-dihydro-5H-thiazolo[3,2-c]-pyrimidine-5,7(6H)-dione

Thionyl chloride (0.61 ml)was added dropwise to a solution of 2-hydroxymethyl-6-propyl-2,3-dihydro-5H-thiazolo[3,2-c]pyrimidine-5,7(6H)-dione (1 g) in methylene chloride (15 ml) with stirring at room temperature, and the solution was refluxed for 16 hours. The solution was concentrated to dryness, and the resulting residue was purified by column chromatography on silica gel. The resulting crude crystals were recrystalized from methylene chloride-isopropyl ether to give colorless crystals (0.9 g, 84%).

Melting point: 85°-88° C.

| Elemental analysis for $C_{10}H_{13}ClN_2O_2S$ | | | |
| --- | --- | --- | --- |
|  | C(%) | H(%) | N(%) |
| Calcd: | 46.06 | 5.03 | 10.74 |
| Found: | 46.08 | 5.03 | 10.74 |

$^1$H-NMR(CDCl$_3$)δ: 0.92(3H,t),1.41-1.87(2H,m), 3.63-4.22(1H,m),3.73(2H,s),3.82(2H,t), 4.33(1H,q), 5.68(1H,s)

EXAMPLE 122

2-Chloromethyl-8-phenyl-6-propyl-2,3-dihydro-5H-thiazolo[3,2-c]pyrimidine-5,7(6H)-dione The compound was obtained by a method similar to that of Example 121.

Melting point: 112°-113° C.

| Elemental analysis for $C_{16}H_{17}ClN_2O_2S$ | | | |
| --- | --- | --- | --- |
|  | C(%) | H(%) | N(%) |
| Calcd: | 57.05 | 5.09 | 8.32 |
| Found: | 57.07 | 5.13 | 8.47 |

1H-NMR(CDCl3)δ: 0.95(3H,t),1.49–1.93(2H,m),
3.55–4.10(1H,m),3.66(2H,s),4.45(1H,q),
7.38(5H,s).

EXAMPLE 123

2-Phenylthiomethyl-6-propyl-2,3-dihydro-5H-thiazolo[3,2-c]pyrimidine-5,7(6H)-dione A mixture of 2-chloromethyl-6-propyl-2,3-dihydro-5H-thiazolo[3,2-c]pyrimidine-5,7(6H)-dione (0.8 g), thiophenol (0.47 ml) and potassium carbonate (0.63 g) was refluxed in ethanol (20 ml) for 42 hours. The solution was concentrated to dryness, and the resulting residue thus obtained was dissolved in methylene chloride and water. After washing with water and drying, the organic solution was concentrated to dryness. The resulting syrup was purified by column chromatography on silica gel to give colorless syrup. This syrup was allowed to stand in a refrigerator to obtain colorless crystals (1.2 g, 95%).

Melting point: 88°–89° C.

| Elemental analysis for $C_{16}H_{18}N_2O_2S$: | | | |
|---|---|---|---|
| | C(%) | H(%) | N(%) |
| Calcd: | 57.46 | 5.42 | 8.38 |
| Found: | 57.56 | 5.45 | 8.40 |

1H-NMR(CDCl3)δ:
0.92(3H,t),1.41–1.86(2H,m),3.17(2H,d),
3.83(2H,t),4.28,4.31(each 1H,d),
5.63(1H,s),7.27–7.53(5H,m)

EXAMPLE 124

2-Methylene-6-propyl-2,3-dihydro-5H-thiazolo[3,2-c]pyrimidine-5,7(6H)-dione

Piperidine (0.66 g) and potassium iodide (0.1 g) were added to a solution of 2-chloromethyl-6-propyl-2,3-dihydro-5H-thiazolo[3,2-c]pyrimidine-5,7(6H)-dione (1g) in ethanol (20 ml). The reaction mixture was stirred at 60° C. for 42 hours. The reaction solution was concentrated to dryness, and the residue was dissolved in chloroform. After washing with water and drying, the organic layer was concentrated to dryness. The resulting residue was purified by column chromatography on silica gel. The resulting crystals were recrystallized from methylene chloride-isopropyl ether-hexane to give colorless crystals (0.55 g, 64%).

Melting point: 102°–103° C.

| Elemental analysis for $C_{10}H_{12}C_1N_2O_2S$: | | | |
|---|---|---|---|
| | C(%) | H(%) | N(%) |
| Calcd: | 53.55 | 5.39 | 12.49 |
| Found: | 53.66 | 5.37 | 12.46 |

1H-NMR(CDCl3)δ:
0.93(3H,t),1.41–1.88(2H,m),3.84(2H,t),
4.89(2H,t),5.29(1H,q),5.42(1H,q),
5.65(1H,s)

EXAMPLE 125

Ethyl (3-amino-6,8-dioxo-7-propyl-4H,6H-pyrimido[6,1-b][1,3]thiazine-2-yl)carboxylate A solution of 6-chloro-1-cyanomethyl-3-propyl-pyrimidine-2,4(1H,3H)-dione (1.5 g), ethyl thioglycolate (0.88 g) and potassium carbonate (1 g) in ethanol (30 ml) was refluxed for 15 hours. The reaction solution was concentrated to dryness, and the resulting residue was purified by column chlomatography on silica gel. The resulting crude crystals were recrystalized from ethyl acetate-hexane to give colorless plates (0.23 g, 11%).

Melting point: 200°–201° C.

| Elemental analysis for $C_{13}H_{17}N_3O_4S$ | | | |
|---|---|---|---|
| | C(%) | H(%) | N(%) |
| Calcd: | 50.15 | 5.50 | 13.50 |
| Found: | 50.32 | 5.52 | 13.40 |

1H-NMR(200MHz, CDCl3)δ:
0.94(3H,t),1.33(3H,t),1.56–1.73
(2H,m),3.87(2H,t),4.24(2H,q),
4.64(2H,s),5.97(1H,s).

EXAMPLE 126

Ethyl (3-amino-6,8-dioxo-9-phenyl-7-propyl-7,8-dihydro-4H,6H-pyrimido[6,1-b][1,3]thiazine-2-yl)carboxylate The compound was synthesized by a method similar to that of Example 125 in a 39% yield.

Melting point: 172°–173° C.

| Elemental analysis for $C_{19}H_{21}N_3O_4S$ | | | |
|---|---|---|---|
| | C(%) | H(%) | N(%) |
| Calcd: | 58.90 | 5.46 | 10.85 |
| Found | 58.67 | 5.52 | 10.53 |

1H-NMR(200MHz, CDCl3)δ:
0.96(3H,t),1.21(3H,t),1.60–1.79
(2H,m),3.94(2H,t),4.15(2H,q),
4.77(2H,s),7.30–7.48(5H,m).

EXAMPLE 127

9-Phenyl-7-propyl-4H,6H-pyrimido[6,1-b][1,3]thiazine6,8(7H)-dione

A catalytic amount of p-toluenesulfonic acid was added to a solution of 2-hydroxy-9-phenyl-7-propyl-3,4-dihydro2H,6H-pyrimido[6,1-b][1,3]thiazine-6,8(7H)-dione (0.5 g) in toluene (20 ml) and was refluxed for 5 hours. The reaction solution was concentrated to dryness, and the resulting residue was dissolved in methylene chloride. After washing with water and drying, the solution was concentrated to dryness. The resulting crude crystals were recrystalized from ethyl acetate-isopropyl ether to give colorless prisms (0.33 g, 70%).

Melting point: 142°–144° C.

| Elemental analysis for $C_{16}H_{16}N_2O_2S$ | | | |
|---|---|---|---|
| | C(%) | H(%) | N(%) |
| Calcd: | 63.98 | 5.37 | 9.33 |
| Found: | 63.82 | 5.52 | 9.15 |

1H-NMR(CDCl3)δ: 0.96(3H,t),1.61–1.80(2H,m),
3.95(2H,t),4.61(2H,d),6.31–6.43(2H,m),
7.26–7.48(5H,m)

EXAMPLES 128 and 129

The following compounds were synthesized by methods similar to that of Example 127.

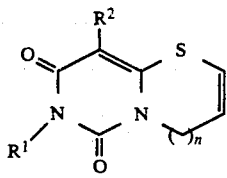

| Example No. | R¹ | R² | n | Yield (%) | m.p. (°C.) | ¹H-NMR (δ) |
|---|---|---|---|---|---|---|
| 128 | Bu | Ph | 1 | 80 | 131–132 | (CDCl₃); 0.94(3H, t), 1.31–1.48(2H, m), 1.55–1.73(2H, m), 4.00(2H, t), 4.61(2H, d), 6.31–6.44(2H, m), 7.27–7.48(5H, m). |
| 129 | Bzl | Ph | 1 | 78 | 161–164 | (CDCl₃); 4.59(2H, d), 5.18(2H, s), 6.28–6.42(2H, m), 7.26–7.58(10H, m). |

EXAMPLE 130

7-Benzyl-9-phenyl-4H,6H-pyrimido[6,1-b][1,3]thiazine-6,8(7H)-dione

Trifluoroacetic acid anhydride (5.17 g) was added to a solution of 7-benzyl-1-oxo-9-phenyl-3,4-dihydro-4H,6H-pyrimido[6,1-b][1,3]thiazine-6,8(7H)-dione (3 g) in toluene (90 ml) and the mixture was refluxed for 15 hours. The reaction solution was concentrated to dryness, and the resulting residue was purified by column chlomatography on silica gel. The resulting crude crystals were recrystalized from methylene chloride-isopropyl ether to give colorless crystals (2.22 g, 78%).

Melting point: 161°–164° C.

| Elemental analysis for $C_{20}H_{16}N_2O_2S$: | | | |
|---|---|---|---|
| | C(%) | H(%) | N(%) |
| Calcd: | 68.94 | 4.63 | 8.04 |
| Found: | 69.16 | 4.67 | 7.99 |

¹H-NMR(200MHz, CDCl₃)δ: 4.59(2H,d), 5.18(2H,s), 6.28–6.42(2H,m), 7.26–7.58(10H,m)

EXAMPLES 131 TO 137

The following compounds were synthesized by methods similar to that of Example 130.

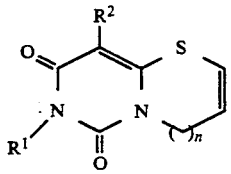

| Example No. | R¹ | R² | n | Yield (%) | m.p. (°C.) | ¹H-NMR (200 MHz, CDCl₃) δ |
|---|---|---|---|---|---|---|
| 131 | Pen | Ph | 1 | 73 | 95–96 | 0.89(3H, t), 1.30–1.41(4H, m), 1.61–1.75(2H, m), 3.98(2H, t), 4.61(2H, d), 6.30–6.43(2H, m), 7.25–7.30(2H, m), 7.36–7.48(3H, m). |
| 132 | Hex | Ph | 1 | 87 | 81–82 | 0.87(3H, t), 1.21–1.45(6H, m), 1.58–1.74(2H, m), 3.98(2H, t), 4.60(2H, d), 6.29–6.43(2H, m), 7.25–7.31(2H, m), 7.37–7.48(3H, m). |
| 133 | Hep | Ph | 1 | 95 | Syrup | 0.87(3H, t), 1.22–1.44(8H, m), 1.58–1.75(2H, m), 3.98(2H, t), 4.61(2H, d), 6.30–6.44(2H, m), 7.26–7.32(2H, m), 7.37–7.49(3H, m). |
| 134 | —CH₂—C₆H₄—OMe (o) | Ph | 1 | 96 | Syrup | 3.78(3H, s), 4.59(2H, d), 5.15(2H, s), 6.28–6.41(2H, m), 6.78–6.84(1H, m), 7.07–7.30(5H, m), 7.37–7.48(3H, m). |
| 135 | —CH₂—C₆H₄—OMe (p) | Ph | 1 | 94 | 162–163 | 3.78(3H, s), 4.58(2H, d), 5.11(2H, s), 6.27–6.40(2H, m), 6.83(2H, dd), 7.27(2H, dd), 7.37–7.55(5H, m). |
| 136 | —CH₂—C₆H₄—Cl (o) | Ph | 1 | 77 | 231–232 | 4.62(2H, d), 5.32(2H, s), 6.30–6.44(2H, m), 7.10–7.23(3H, m), 7.28–7.48(6H, m). |

-continued

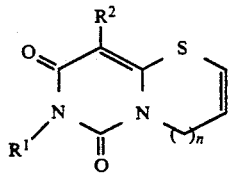

| Example No. | R¹ | R² | n | Yield (%) | m.p. (°C.) | ¹H-NMR (200 MHz, CDCl₃) δ |
|---|---|---|---|---|---|---|
| 137 | 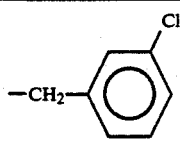 | Ph | 1 | 75 | 142–143 | 4.60(2H, d), 5.13(2H, s), 6.29–6.42(2H, m), 7.21–7.30(4H, m), 7.32–7.52(5H, m). |

EXAMPLE 138

9-Phenyl-4H,6H-pyrimido[6,1-b][1,3]thiazine-6,8(7H)-dione

Boron trifluoride (0.7 ml) was added to a solution of 7-benzyl-9-phenyl-4H,6H-pyrimido[6,1-b][1,3]thiazine-6,8(7H)-dione (1 g) in toluene (25 ml) and the mixture was refluxed for 15 hours. Methanol (7.5 ml) was added to the reaction solution at room temperature and the solution was stirred for 30 minutes. The reaction solution was concentrated to dryness, and acetone was added to the resulting residue to obtain the presipitate by filtration. The resulting crude crystals were washed and recrystallized from DMF-water to give yellow needles (0.13 g, 18%).

Melting point: 286°–290° C.

| Elemental analysis for C₁₃H₁₀N₂O₂S: | | | |
|---|---|---|---|
| | C(%) | H(%) | N(%) |
| Calcd: | 60.45 | 3.90 | 10.85 |
| Found: | 60.51 | 4.02 | 10.82 |

¹H-NMR(200MHz, CDCl₃)δ: 4.43(2H,dd),6.41(1H,dt), 6.62(1H,dt),7.18–7.25(2H,m), 7.34–7.46(3H,m).

EXAMPLE 139

Ethyl 4-(6,8-dioxo-9-phenyl-7,8-dihydro-4H,6H-pyrimido[6,1-b][1,3]thiazine-7-yl)butylate A mixture of 9-phenyl-4H,6H-pyrimido[6,1-b][1,3]thiazine-6,8(7H)-dione (0.9 g), ethyl 4-bromobutylate (1.02 g) and potassium carbonate (0.58 g) in DMF (15 ml) was stirred at 90° C. for 15 hours. The reaction solution was concentrated to dryness, and the residue was purified by column chromatography on silica gel. The resulting crude crystals were recrystalized from ethyl ether to give colorless crystals (0.9 g, 69%).

Melting point: 85°–86° C.

| Elemental analysis for C₁₉H₂₀N₂O₄S: | | | |
|---|---|---|---|
| | C(%) | H(%) | N(%) |
| Calcd: | 61.27 | 5.41 | 7.52 |
| Found: | 61.49 | 5.43 | 7.52 |

¹H-NMR(200MHz, CDCl₃)δ: 1.24(3H,t),1.95–2.10(2H,m), 2.39(2H,t),4.07(2H,t),4.12(2H,q),4.61(2H,d), 6.32–6.44(2H,m),7.24–7.31(2H,m),7.37–7.49(3H,m).

EXAMPLE 140

7-(p-Methylbenzyl)-9-phenyl-4H,6H-pyrimido-[6,1-b][1,3]thiazine-6,8(7H)-dione

A mixture of 9-phenyl-4H,6H-pyrimido[6,1-b][1,3]thiazine-6,8(7H)-dione (0.26 g), p-methylbenzyl-chloride (0.21 g) and potassium carbonate (0.28 g) in DMF (5 ml) was stirred at 100° C. for 15 hours. The reaction solution was concentrated to dryness. The resulting residue was dissolved in dichloroethane and was washed with water and dried. m-Chloroperbenzoic acid (0.2 g) was added to the dichloroethane solution little by little under ice cooling, and it was allowed to stand at room temperature for 15 hours. The reaction solution was washed with saturated aq. sodium bicarbonate, and dried, and then trifluoro acetic acid anhydride (0.5 ml) was added thereto and the mixture was refluxed for 15 hours. Oily product obtained by concentration of the resulting solution was dissolved in toluene (20 ml), and a catalytic amount of p-toluene sulfonic acid was added thereto and the mixture was refluxed for 10 hours. The reaction solution was washed with sodium bicarbonate and water, followed by concentration to dryness. The obtained crude crystals were recrystallized from ethyl ether to give colorless crystals (0.12 g, 33%).

Melting point: 124°–125° C.

| Elemental analysis for C₂₁H₁₈N₂O₄S | | | |
|---|---|---|---|
| | C(%) | H(%) | N(%) |
| Calcd: | 68.91 | 5.07 | 7.65 |
| Found: | 68.75 | 4.87 | 7.51 |

¹H-NMR(200MHz, CDCl₃)δ: 2.31(3H,s),4.57(2H,d), 5.13(2H,s),6.25–6.42(2H,m),7.05–7.50(9H,m).

EXAMPLES 141 TO 155

The following compounds were synthesized by methods similar to that of Example 140.

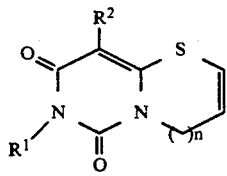
| Example | R¹ | R² | n | Yield (%) | m. p. (°C.) | ¹H-NMR(200MHz, CDCl₃)δ |
|---|---|---|---|---|---|---|
| 141 | CH₂CN | Ph | 1 | 34 | 159–160 | 4.63(2H, q), 4.89(2H, s) 6.35–6.45(2H, m), 7.20–7.50(5H, m), |
| 142 | —CH₂COOEt | Ph | 1 | 60 | 174–175 | 1.29(3H, t), 4.23(2H, q), 4.61(2H, d), 4.74(2H, s), 6.35–6.45(2H, m), 7.20–7.50(5H, m). |
| 143 | —CH₂—C₆H₄—F | Ph | 1 | 45 | 178–179 | 4.59(2H, d), 5.14(2H, s), 6.30–6.45(2H, m), 6.70(1H, m), 7.20–7.60(8H, m). |
| 144 | —CH₂—C₆H₄—F (o-F) | Ph | 1 | 82 | 182–183 | 4.61(2H, m), 5.28(2H, s), 6.30–6.45(2H, m), 7.05(2H, m), 7.25–7.50(7H, m). |
| 145 | —CH₂—C₆H₄—Me (o-Me) | Ph | 1 | 21 | 165–167 | 2.47(3H, s), 4.61(2H, d), 5.20(2H, s), 6.25–6.45(2H, m), 7.10–7.50(9H, m). |
| 146 | —CH₂—C₆H₄—NO₂ | Ph | 1 | 57 | 200–201 | 4.60(2H, d), 5.24(2H, s), 6.30–6.45(2H, m), 7.27(2H, m), 7.41(3H, m), 7.68(2H, d), 8.16(2H, d). |
| 147 | —CH₂—C₆H₄—Cl | Ph | 1 | 57 | 173–174 | 4.59(2H, m), 5.13(2H, s), 6.25–6.40(2H, m), 7.26(2H, m), 7.35–7.55(7H, m). |
| 148 | —CH₂—C₆H₄—NO₂ (o-NO₂) | Ph | 1 | 56 | 203–204 | 4.60(2H, d), 5.58(2H, s) 6.30–6.45(2H, m), 7.20–7.60(8H, m), 8.02(1H, d). |
| 149 | —CH₂—C₆H₃(OMe)₂ | Ph | 1 | 42 | 154–155 | 3.86(3H, s), 3.87(3H, s), 4.59(2H, d), 5.12(2H, s), 6.25–6.45(2H, m), 6.80(1H, m), 7.10–7.50(8H, m). |
| 150 | —CH₂—C₆H₄—C₆H₄—CN | Ph | 1 | 91 | 180–188 | 4.62(2H, d), 5.23(2H, s), 6.25–6.45(2H, m), 7.20–7.80(13H, m), |
| 151 | —CH₂CH₂—C₆H₅ | Ph | 1 | 61 | 145–147 | 2.90–3.05(2H, m), 4.10–4.30(2H, m), 4.62(2H, d), 6.30–6.45(2H, m), 7.20–7.50(10H, m). |

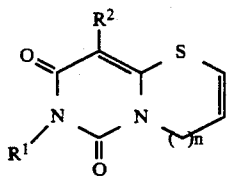

| Example | R¹ | R² | n | Yield (%) | m. p. (°C.) | $^1$H-NMR(200MHz, CDCl$_3$)δ |
|---|---|---|---|---|---|---|
| 152 | -CH₂-(3-pyridyl) | Ph | 1 | 23 | 166-168 | 4.62(2H, s), 5.33(2H, s), 6.30-6.45(2H, m), 7.15(1H, m), 7.20-7.50(6H, m), 7.62(1H, m), 8.55(1H, m). |
| 153 | -CH₂-(4-pyridyl) | Ph | 1 | 11 | 173-175 | 4.61(2H, d), 5.16(2H, s), 6.30-6.45(2H, m), 7.20-7.55(7H, m), 8.55(2H, m). |
| 154 | -CH₂-(2-naphthyl) | Ph | 1 | 50 | 201-202 | 4.59(2H, d), 5.68(2H, s), 6.25-6.40(2H, m), 7.20-7.60(9H, m), 7.83(2H, m), 8.32(1H, d). |
| 155 | -CH₂-(2-quinolyl) | Ph | 1 | 41 | 140-142 | 4.64(2H, d), 5.51(2H, s), 6.30-6.45(2H, m), 7.20-7.80(9H, m), 8.07(2H, t). |

The following compounds were synthesized by methods similar to that of Example 130.

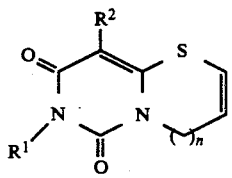

| Example No. | R¹ | R² | n | Yield (%) | m.p. (°C.) | $^1$H-NMR (200 MHz, CDCl$_3$) δ |
|---|---|---|---|---|---|---|
| 156 | Pr | Ph | 0 | 73 | 144-145 | 0.99(3H, t), 1.66-1.84(2H, m), 4.05(2H, t), 6.46(1H, d), 7.64(1H, d), 7.31-7.56(5H, m). |
| 157 | Pr | Ph | 2 | 31 | 156-157 | 0.96(3H, t), 1.61-1.80(2H, m), 2.64-2.73(2H, m), 3.94(2H, t), 4.74(2H, t), 5.82(1H, dt), 5.97(1H, dt), 7.18-7.26(2H, m), 7.35-7.44(3H, m). |
| 158 | Pr | H | 1 | 54 | Syrup | 0.94(3H, t), 1.57-1.74(2H, m), 3.89(2H, t), 4.50(2H, d), 5.83(1H, s), 6.34(1H, dt), 6.41(1H, dt). |
| 159 | Pr | COCF₃ | 1 | 10 | 137-138 | 0.96(3H, t), 1.58-1.77(2H, m), 3.89(2H, t), 4.50(2H, d), 5.83(1H, s), 6.34(1H, dt), 6.41(1H, d). |

The following compounds were synthesized by the methods similar to that of Example 83.

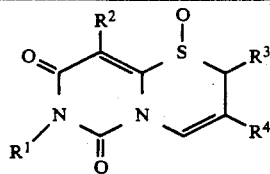

| Example No. | R¹ | R² | R³ | R⁴ | Yield (%) | m. p. (°C.) | ¹H-NMR(200MHz, CDCl₃)δ |
|---|---|---|---|---|---|---|---|
| 160 | Pr | Ph | H | CH₃ | 70 | 168–171 | 0.97(3H, t), 1.62–1.80(2H, m) 2.06(3H, d), 3.37(1H, dq), 3.62(1H, d), 3.99(2H, t), 7.43–7.50(6H, m). |
| 161 | Bu | Ph | H | H | 85 | 179–180 | 0.96(3H, t), 1.31–1.49(2H, m), 1.56–1.75(2H, m), 3.35(1H, dt), 3.84(1H, dd), 4.04(2H, dt), 5.57(1H, dt), 7.48(5H, s), 7.71(1H, dd). |
| 162 | −CH₂−C₆H₅ | Ph | H | H | 83 | 185–186 | 3.31(1H, dt), 3.81(1H, dd), 5.21(2H, s), 5.51–5.60(1H, m), 7.20–7.57(10H, m), 7.69(1H, dd). |
| 163 | −CH₂−C₆H₄(OMe) | Ph | H | H | 88 | 192–193 | 3.31(1H, dt), 3.79(3H, s), 3.82(1H, dd), 5.18(2H, s), 5.51–5.61(1H, m), 6.82–6.87(1H, m), 7.08–7.53(8H, m), 7.68(1H, dd). |
| 164 | −CH₂−C₆H₄(Cl) | Ph | H | H | 83 | 203–204 | 3.34(1H, dt), 3.83(1H, dd), 5.16(2H, s), 5.53–5.63(1H, m), 7.21–7.31(2H, m), 7.37–7.53(7H, m), 7.69(1H, dd). |

EXAMPLE 165

2-Hydroxy-1-oxo-3-methyl-9-phenyl-7-propyl-3,4-dihydro-2H,6H-pyrimido[6,1-b][1,3]thiazine-6,8(7H)-dione The compound was synthesized by a method similar to that of Example 78 in a 58% yield.
Melting point: 185°–186° C.
NMR(200MHz, CDCl₃)δ: 0.95(3H,t),1.17(3H,d), 1.59–1.79(2H,m),2.20–2.44(1H,m),2.75(1H, brs), 3.58–3.79(1H,m), 3.94(2H,t),4.36(1H,dd), 4.91–5.05(1H,m), 7.20–7.29(2H,m),7.35–7.46(3H,m).

EXAMPLE 166

7-Benzyl-9-phenyl-2H,6H-pyrimido[6,1-b][1,3]thiazine-6,8(7H)-dione

Phosphorus trichloride (0.2 ml) was added dropwise to a solution of 7-benzyl-1-oxo-9-phenyl-2H,6H-pyrimido[6,1-b]-[1,3]thiazine-6,8(7H)-dione (0.4 g) in DMF (8 ml) under stirring at −10° C. The mixture was stirred at the same temperature for 30 minutes and the resulting solution was poured to ice-water to give crystals and the crystals were collected by filtration. The resulting crude crystals were washed and recrystalized from methylene chloride-methanol to give colorless needles (0.31 g, 81%).

Melting point: 202°–203° C.

| Elemental analysis for C₂₀H₁₆N₂O₂S | | | |
|---|---|---|---|
|  | C(%) | H(%) | N(%) |
| Calcd: | 68.94 | 4.63 | 8.04 |
| Found: | 68.33 | 4.78 | 7.92 | the following compounds were synthesized by a method similar to that of Example 166.

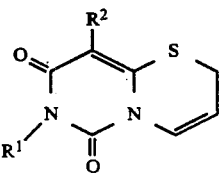

| Example No. | R¹ | R² | Yield (%) | m.p. (°C.) | ¹H-NMR(200MHz, CDCl₃)δ |
|---|---|---|---|---|---|
| 167 | Pr | Ph | 48 | 167–168 | 0.96(3H, t), 1.30–1.48(2H, m), |

-continued
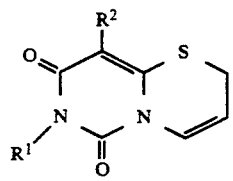
| Example No. | R$^1$ | R$^2$ | Yield (%) | m.p. (°C.) | $^1$H-NMR(200MHz, CDCl$_3$)δ |
|---|---|---|---|---|---|
| 168 | Bu | Ph | 50 | 88–89 | 1.60–1.74(2H, m), 3.26(2H, dd), 4.01(2H, t), 5.63(1H, dt), 7.25–7.32(2H, m), 7.37–7.49(4H, m). 0.95(3H, t), 1.30–1.48(2H, m), 1.60–1.74(2H, m), 3.26(2H, dd), 4.01(2H, t), 5.63(1H, dt), 7.25–7.32(2H, m), 7.37–7.49(4H, m). |
| 169 | —CH$_2$—C$_6$H$_4$—OMe | Ph | 78 | 111–112 | 3.25(2H, dd), 3.79(3H, s), 5.17(2H, s), 5.62(1H, dt), 6.79–6.86(1H, m), 7.08–7.31(6H, m), 7.37–7.48(3H, m). |
| 170 | —CH$_2$—C$_6$H$_4$—Cl | Ph | 83 | 166–167 | 3.27(2H, dd), 5.15(2H, s), 5.64(1H, dt), 7.23–7.31(4H, m), 7.38–7.54(6H, m). |
| 171 | —CH$_2$—C$_6$H$_4$—Cl | Ph | — | — | — |
| 172 | —CH$_2$—C$_6$H$_4$—Cl | Ph | — | — | — |
| 173 | —CH$_2$—C$_6$H$_4$—OMe | Ph | — | — | — |
| 174 | —CH$_2$—C$_6$H$_4$—NO$_2$ | Ph | — | — | — |
| 175 | —CH$_2$—C$_6$H$_4$—NO$_2$ | Ph | — | — | — |
| 176 | —CH$_2$—C$_6$H$_4$—CH$_3$ | Ph | — | — | — |
| 177 | —CH$_2$—C$_6$H$_4$—F | Ph | — | — | — |

-continued

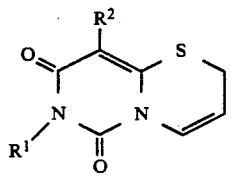

| Example No. | R¹ | R² | Yield (%) | m.p. (°C.) | ¹H-NMR(200MHz, CDCl₃)δ |
|---|---|---|---|---|---|
| 178 | −CH₂−⟨C₆H₃⟩(OMe)(OMe) | Ph | — | — | — |
| 179 | −CH₂−⟨C₆H₄⟩−⟨C₆H₄⟩−NC | Ph | — | — | — |

EXAMPLE 180

3-Methyl-9-phenyl-7-propyl-4H,6H-pyrimido[6,1-b][1,3]-thiazine-6,8(7H)-dione

The compound was synthesized by a method similar to that of Example 127 in a 70% yield.
Melting point: 146°–147° C.
NMR(200MHz, CDCl₃)δ:
0.96(3H,t),1.61–1.80(2H,m),
2.04(3H,s), 3.96(2H,t),4.51(2H,s),5.98(1H,s),
7.25–7.30(2H,m), 7.36–7.48(3H,m).

PREPARATION EXAMPLES

When the compounds of the present invention are used as therapeutic preparations for diseases such as myocardial infarction, angina pectoris, renal failure, chronic rheumatism asthma, cerebral lesion and impairment of memory, they can be prepared in accordance with, for example, the following formulations:

| 1. Tablet | |
|---|---|
| (1) 9-Phenyl-7-propyl-4H,6H-pyrimido[6,1-b][1,3]-thiazine-6,8(7H)-dione | 10 mg |
| (2) Lactose | 35 mg |
| (3) Cornstarch | 150 mg |
| (4) Microcrystalline cellulose | 30 mg |
| (5) Magnesium stearate | 5 mg |
| | 230 mg |

(1), (2), (3), two thirds of (4) and one half of (5) are mixed and then granulated. The remainders of (4) and (5) are added to the granules, and the mixture is pressed to form a tablet.

| 2. Capsule | |
|---|---|
| (1) 9-Phenyl-7-butyl-4H,6H-pyrimido[6,1-b][1,3]-thiazine-6,8(7H)-dione | 10 mg |
| (2) Lactose | 100 mg |
| (3) Microcrystalline cellulose | 70 mg |
| (4) Magnesium stearate | 10 mg |
| | 190 mg |

(1), (2), (3) and one half of.(4) are mixed, and then granulated. The remainder of (4) is added to the granules, and the whole is encapsulated in a gelatin capsule.

| 3. Ointment | |
|---|---|
| (1) 1,1-Dioxo-9-phenyl-7-propyl-3,4-dihydro-2H,6H-pyrimido[6,1-b][1,3]thiazine-6,8(7H)-dione | 2.5 g |
| (2) Macrogoal 400 | 70.0 g |
| (3) Macrogoal 4000 | 27.5 g |
| | 100.0 g |

(2) and (3) are heated, and (1) is dissolved therein, followed by gradual cooling with stirring to form an ointment.

EXPERIMENT 1

Inhibitory Effects of the Compounds on Endothelium Induced Contraction in Porcine Coronary Arteries (Process)

Ring preparation of porcine left arterior descending coronary arteries (LAD) were suspended in 20 ml baths containing Krebs-Henseleit solutions at 37° C. gassed with 97% $O_2$–3% $CO_2$. Endothelin ($3\times10^{-9}$ M) was added to the baths, and after the constriction reached the steady state, the compounds at concentrations of $1^{-6}$ and $10^{-5}$ M (Examples 45, 48 and 127) were added to the bath. Then, the relaxation activity was examined. The relaxation activity of the compounds was expressed as % inhibition from the maximum contraction by endothelin.

(Results)

The results are shown in Table 1. As shown in Table 1, the following compounds inhibited the endothelin constriction at concentrations of $10^{-6}$ M and $10^{-5}$ M in a concentration dependent manner.

TABLE 1

| Example No. | Inhibition (%) | |
| --- | --- | --- |
| | $10^{-6}$ | $10^{-5}$ (M) |
| 45 | 6.2 | 100 |
| 48 | 24.6 | 86.6 |
| 127 | 82.3 | 90.0 |

EXPERIMENT 2

Inhibitory Effects on Endothelin Induced Pressor and Depressor Responses in Conscious Beagle Dogs (Process)

Using 10 male beagles (12–14 kg, 8–10 months old), a polyethylene cannula (PEG-100) was inserted into each of the left femoral artery and vein of each beagle after pentobarbital anesthesia. The experiment was started from 3 to 7 days after the operation. The cannula was connected to a pressure transducer to measure the systemic blood pressure. The endothelin antagonistic activity of the compound obtained in Example 65 was examined, taking the depressor and pressor responses due to the intravenous administration of endothelin as its indication. The compound was orally or intravenously administered 5 minutes before the administration of endothelin.

(Results)

When 100 pmol/kg of endothelin was intravenously administered, the systemic blood pressure transiently reduced (about 30 mm Hg), and then gradually increased (about 20 mm Hg). As shown below, the intravenous administration of the compound at a dose of 1 mg/kg (Table 2) and the oral administration of the compound in a dose of 10 mg/kg (Table 3) significantly inhibited the depressor and pressor responses due to endothelin. Its inhibitory activity was continuously sustained, for 6 hours by the intravenous administration (i. v.) and for more than 8 hours in the oral administration (p. o.).

TABLE 2

| Elapsed Time After Administration | Compound (127) (1 mg/kg, i.v.) | | | | |
| --- | --- | --- | --- | --- | --- |
| | 5 min | 1 hr | 2 hr | 4 hr | 6 hr |
| Pressor Response | 100 | 55 ± 7 | 55 ± 7 | 38 ± 15 | 32 ± 10 |
| Depressor Response | 86 ± 9 | 74 ± 11 | 57 ± 10 | 31 ± 13 | 30 ± 8 |

The numerical values indicate % inhibition ± standard error (%) (n = 4).

TABLE 3

| Elapsed Time After Administration | Compound (127) (10 mg/kg, p.o.) | | | |
| --- | --- | --- | --- | --- |
| | 1 hr | 2 hr | 4 hr | 8 hr |
| Pressor Response | 37 ± 10 | 85 ± 10 | 76 ± 12 | 43 ± 4 |
| Depressor Response | 34 ± 9 | 81 ± 10 | 67 ± 12 | 50 ± 0 |

The numerical values indicate % inhibition ± standard error (%) (n = 3).

EXPERIMENT 3

Depressing Effect Against Evolution of Infarct Size in Ischemic and Reperfused Rat Heart Male Wistar rats were medianly dissected under pentobarbital anesthesia, and left anterior descending coronary artery was occluded at its origin for 1 hour, followed by resumption of Blood flowing. The chest was closed 30 to 60 minutes after the reperfusion, and the rates were kept under conscious state. After 24 hours, the rats were anesthetized again and the hearts were excised. The left ventricle of each heart was divided into six parts, and these divided parts were stained with 1% triphenyltetrazolium chloride solution at 37° C. for 15 minutes. Then, infarcted portions were weighed.

The compound obtained in Example 127 was orally administered in a dose of 100 mg/kg as a gum arabic suspension 2 hours before the occlusion and 5 hours after the reperfusion.

(Results)

The results are shown in Table 4. As shown in Table 4, with respect to a control group (N=12), the myocardial infarct size was 36.7±1.4% of the weight of left ventricles. In contrast, in treated group, myocardial infarct size was significantly reduced, showing the size of 26.8±3.1%.

TABLE 4

| Control Group | Compound (127)-Administered Group |
| --- | --- |
| 36.7 ± 1.4 (12) | 26.8 ± 3.1 **(5) |

The numerical values indicate the ratio of the weight of the infarcted region to the weight of the left ventricles ± standard error (%). The numerical values in parentheses indicate the number of experiments.
**P < 0.01 (vs. control)

EXPERIMENT 4

Inhibitory Effects on Interleukin 1 Production Simulated by Lipopolysaccharide in the Rat Intraperitoneal Macrophage (Process)

Male Sprague-Dawley rats (8 weeks old, body weight: 300 g, Clea Japan) were killed by exsanguination under etherization. 20 ml of a culture solution (RPMI-1640) was intraperitoneally administered to each rat, and the abdominal part thereof was massaged, followed by abdominal section to recover the culture solution. After centrifugation of the solution, the cell pellet obtained was resuspended in 4 ml of the culture solution, superposed on 5 ml of Ficoll-Paque solution (lymphocyte separation medium, Wako Junyaku, Japan), and centrifuged at 450 g at room temperature for 15 minutes. The cells located in the boundary between the Ficoll-Paque solution and the culture solution were collected and washed 3 times with the culture solution. The resulting cells were suspended in the culture solution again, which was used as a macrophage-suspended solution ($3 \times 10^5$ cells/ml).

Interleukin 1 was produced in the following manner. Macrophage ($3 \times 10^5$ cells) in a 96-well microtiter plate was preincubated in a $CO_2$ incubator for 1 hour with each of the compounds shown in Table 5. Then, 50 ug/ml of lipopolysaccharide (*Escherichia coli* 0111 B4, Difco) was added thereto. After cultivation was further continued for 20 hours, the activity of interleukin 1 in the culture supernatant was measured by an LAF (lymphocyte activating factor) assay. Experiments were carried out in a triplicate manner.

The LAF assay was conducted as the following. Thymocytes ($1–1.5 \times 10^6$ cells) of C3H/HeJ mice were added to phytohemagglutinin (PHA) P (diluted 1/2000;

Difico) and the macrophage culture solution diluted 1/10 or 1/30, and cultivated in a $CO_2$ incubator. After 48 hours, $^3$H-thymidine of 0.5 uCi was added thereto and cultivation was further continued for 24 hours. Then, the amount of $^3$H-thymidine entrapped in the thymocytes was measured. The radioactivity entrapped in the thymocytes was taken as the amount of interleukin-1.

We conducted this process partly modifying the method of R. C. Newton et al. [J. Leukocyte, Biology 39, 299-3111 (1986)].

(Results)

The results are shown in Table 5. As shown in Table 5, it was found that the following compounds had the inhibitory effects on the production of interleukin 1 in the lipopolysaccharide-stimulated rat intraperitoneal macrophage.

TABLE 5

| Example No. | Inhibition (%) | | |
|---|---|---|---|
| | $10^{-5}$ | $10^{-6}$ | (Molar Concentration) |
| 17 | 93 | NT | |
| 43 | 52 | NT | |
| 45 | 75 | 30 | |
| 50 | 98 | 58 | |
| 59 | 89 | NT | |
| 62 | 96 | NT | |
| 63 | 98 | NT | |
| 64 | 100 | 60 | |
| 65 | 100 | 40 | |
| 67 | 98 | 10 | |

EXPERIMENT 5

Activity of Depressing Feverescence of Rat Due to Lipopolvsaccharide (LPS)

(Process)

Male JcL;SD rats 7 weeks old (body weight: about 250 g, Clea Japan) were used. Each group had 6 rats. The rats were reared in individual cages from the day before, and then the basal body temperature was measured in the rectums using a digital thermometer (Model D221-6, Takara Kogyo) 3 times at intervals of 1 hour. After the third measurement of the body temperature, the compounds shown in Table 6 were orally administered in a volume of 1 ml per 100 g of body weight. LPS (Escherichia coli 0111 B4, Difco) was administered from their tail veins in an amount of 0.2 ml per 100 g of body weight 1 hour after the administration of the compounds.

The body temperature was measured from 3 to 5 hours after that at intervals of 1 hour. The antipyretic activity of the compounds was evaluated by the difference in body temperature between a control group and a compound-administered group. Statistical analysis was carried out by the Dunnett's test.

(Results)

the results are shown in table 6. As shown in Table 6, it was found that the following compounds had antipyretic activities in LPS-inducted febrile rats.

TABLE 6

| Example No. | Dose (mg/kg,p.o.) | Antipyretic Activity (°C.) |
|---|---|---|
| 64 | 25 | −0.68** |
| | 50 | −0.82* |

TABLE 6-continued

| Example No. | Dose (mg/kg,p.o.) | Antipyretic Activity (°C.) |
|---|---|---|
| | 100 | −1.13** |
| 23 | 100 | −0.72** |
| 43 | 100 | −0.70** |
| 65 | 100 | −0.95** |
| 101 | 100 | −0.87** |
| 106 | 100 | −0.53* |

*$P < 0.05$ (vs. control)
**$P < 0.01$ (vs. control)

EXPERIMENT 6

Promoting Effects of the Compounds on Synthesis and Secretion of NGF in Glia Cells (Process)

A 48 well-plate was seeded with glia strains cells (C6 glioma) at a rate of $2.5 \times 10^4$ cells/well, which was cultivated in Dulbecco's modified eagle's medium (DMEM) containing 10% fetal calf serum. When the cells became confluent (2 to 3 days), each of the following compounds of the present invention was added thereto, and it was cultivated in serum free-DMEM for 24 hours. NGF secreted in the culture supernatant was assayed by enzyme immuno assay. An amount of NGF is shown in a relative value to 100, the value of control (without addition of the compound). The compounds were added in a solution of DMSO, at an amount of 1/100 (V/V) of a medium (V/V). In a control, DMSO alone was added.

(Results)

As shown in Table 7, the following compounds showed a promoting activity of synthesis and secretion of NGF in a concentration of $10^{-6}$ and $10^{-5}$ M.

TABLE 7

| Example No. | Promoting Activity (%) | |
|---|---|---|
| | $3 \times 10^{-5}$ | $3 \times 10^{-6}$ (M) |
| 1 | 117 ± 34 | 168 ± 6 |
| 36 | 102 ± 2 | 240 ± 16 |
| 58 | 140 ± 2 | 164 ± 25 |
| 61 | 109 ± 12 | 177 ± 8 |
| 129 | 117 ± 6 | 197 ± 9 |

The numerical values indicate average of three times experiments ± standard error.

The following references, which are referred to for their disclosures at various points in this application, are incorporated herein by reference.

Nature 332, 411 (1988)
Mol. Brain Res., 1, 85-92 (1986)
J. Neuroscience, 6, 2155-2162 (1986)
Brain Res., 386, 197-208 (1986)
J. Pham. Sci. 71, 897 (1982)
Xenobiotica 12, 495 (1982)
Arzneim-Forsch. 32, 610 (1982)
J. Chem. Soc., 2385 (1972)
Tetrahedron Lett. 48, 4171 (1977)
Chem. Ber. 95, 1597 (1962)
Ann. Chem. 691, 142 (1966)

What is claimed is:

1. A compound represented by the formula (I) or a pharmacologically acceptable salt thereof:

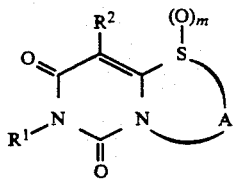

wherein R¹ represents (1) an aliphatic hydrocarbon group which may be substituted by cyano, carbamoyl, heteroaryl, hydroxyl, alkoxy, amino, alkyl, carboxyl, ester or amido group, (2) an aralkyl group which may be substituted by halogen, lower alkyl, phenyl, O-cyanophenyl, alkoxy or nitro group or (3) an aryl group which may be substituted by halogen, lower alkyl, alkoxy or nitro group R² represents (1) hydrogen, (2) an aliphatic hydrocarbon group having one or more substituents selected from cyano, carbamoyl, aryl, hydroxyl, alkoxy, amino, alkyl, carboxyl, ester or amido group, (3) an aryl group which may be substituted by haloge, lower alkyl, alkoxy or nitro group, (4) a group of the formula:

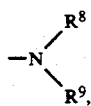

wherein each of R⁸ and R⁹ is hydrogen, a lower alkyl group having about 1 to 8 carbon atoms or a fatty acid-derived acyl group having about 1 to 8 carbon atoms, (5) a formyl group, (6) a nitro group or (7) a halogeno group; A represents (1) a formula:

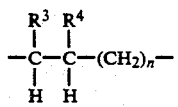

wherein R³ represents hydrogen, a lower alkyl group which may be substituted by halogen atom, lower alkylthio or phenylthio group, —YR wherein Y is —O— or —S— and R⁵ is hydrogen, lower alkyl group of 1 to 4 carbon atoms or an aryl group which may be substituted by alkyl of 1 to 4 carbon atoms, alkoxy of 1 to 4 carbon atoms or phenyl which may be substituted by one to three halogens, or R³ is a fatty acid-derived lower acyl group of 1 to 4 carbon atoms; n represents an integer of 0 to 2, (2) a formula:

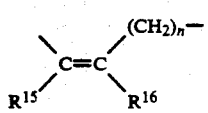

wherein R¹⁵ and R¹⁶ represent hydrogen atoms, lower alkyl group of 1 to 4 carbon atoms, —COOR¹⁷ wherein R¹⁷ is hydrogen atom or lower alkyl, or —NHR¹⁸ wherein R¹⁸ is hydrogen atom, lower alkyl or lower alkanoyl; n represents an integer of 0 to 2 or (3) a formula:

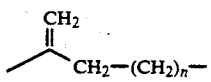

wherein n represents an integer of 0 to 2; and m represents an integer of 0 to 2.

2. The compound according to claim 1, wherein R¹ represents an alkyl group of 1 to 8 carbon atoms, or an alkenyl group of 2 to 8 carbon atoms, which may be substituted by cyano, carbamoyl, heteroaryl, hydroxyl, alkoxy, amino, aklyl, carboxyl, ester or amido group.

3. The compound according to claim 1, wherein R¹ represents an aralkyl group, which is obtained by combining phenyl or naphthyl group with alkylene group of 1 to 4 carbon atoms, in which phenyl or naphthyl group may be substituted by halogen, lower alkyl, lower alkenyl, nitro group or aryl group which may be substituted.

4. The compound according to claim 1, wherein R¹ represents a phenyl or naphthyl group which may be substituted by halogen, lower alkyl, lower alkenyl or nitro group.

5. The compound according to claim 1, wherein R² represents an alkyl group of 1 to 8 carbon atoms or alkenyl group of 2 to 8 carbon atoms, which is substituted by cyano, carbamoyl, aryl, hydroxyl, alkoxy, amino, alkyl, carboxyl, ester or amido group.

6. The compound according to claim 1, wherein R² represents a phenyl or naphthyl group which may be substituted by 1 to 3 halogen, lower alkyl, lower alkoxy or nitro group.

7. The compound according to claim 1, wherein R² represents a group of the formula:

wherein each of R⁸ and R⁹ is hydrogen, a lower alkyl group having about 1 to 8 carbon atoms or a fatty acid-derived acyl group having about 1 to 8 carbon atoms.

8. The compound according to claim 1, wherein R² represents a halogeno group which is selected from the group consisting of fluorine, chlorine, bromine or iodine.

9. The compound according to claim 1, wherein A is represented by the formula

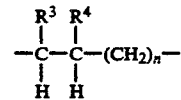

wherein R³ represents hydrogen, an alkyl group which may be substituted, —YR⁵ or a fatty acid-derived lower acyl group of 1 to 4 carbon atoms; R⁴ represents hydrogen or a lower alkyl group of 1 to 4 carbon atoms; and n represents an integer of 0 to 2.

10. The compound according to claim 1, wherein A is represented by the formula:

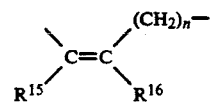

wherein R¹⁵ and R¹⁶ represent hydrogen atoms, lower alkyl groups of 1 to 4 carbon atoms, —COOR¹⁷(R¹⁷ is hydrogen or lower alkyl), or —NHR¹⁸(R¹⁸ is hydrogen, lower alkyl or lower alkanoyl); and n represents an integer of 0 to 2.

11. The compound according to claim 1, wherein A is represented by the formula:

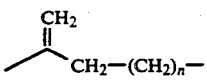

wherein n represents an integer of 0 to 2.

12. The compound according to claim 1, in which $R^1$ is an alkyl group of 3 to 8 carbon atoms or an aralkyl group which may be substituted, $R^2$ is an aryl group which may be substituted, and A is a divalent hydrocarbon chain of 2 to 3 carbon atoms.

13. The pharmacologically acceptable salt of the compounds represented by formula (I) according to claim 1, wherein the salt is an inorganic salt selected from the group consisting of hydrochloride, hydrobromide, sulfate, nitrate and phosphate; or organic salt selected from the group consisting of acetate, tartrate, citrate, fumarate and maleate.

14. The compound according to claim 1, wherein carbon chain number of A is four.

15. The compound according to claim 1, which is 9-phenyl-7-propyl-4H,6H-pyrimido[6,1-b][1,3]thiazine-6,8(7H)-dione.

16. The compound according to claim 1, which is 7-benzyl-9-phenyl-4H,6H-pyrimido[6,1-b][1,3]thiazine-6,8(7H)-dione.

17. The compound according to claim 1, which is 7-(p-chlorobenzyl)-9-phenyl-4H,6H-pyrimido[6,1-b][1,3]thiazine-6,8(7H)-dione.

18. The compound according to claim 1, which is 7-benzyl-9-phenyl-2H,6H-pyrimido[6,1-b][1,3]thiazine-6,8(7H)-dione.

19. The compound according to claim 1, which is 9-phenyl-7-propyl-2H,6H-pyrimido[6,1-b][1,3]thiazine-6,8(7H)-dione.

20. An endotheline inhibiting composition which contains an effective amount of a compound according to claim 1 or a pharmaceutically acceptable salt thereof and pharmaceutically acceptable additional components.

21. An IL-1 inhibiting composition which contains an effective amount of a compound according to claim 1 or a pharmaceutically asceptable salt thereof and pharmaceutically acceptable additional components.

22. An NGF stimulating composition which contains an effective amount of a compound according to claim 1 or a pharmaceutically acceptable salt thereof and pharmaceutically acceptable additional components.

23. A composition according to claim 20, 21 or 22, wherein the pharmaceutically acceptable components include vehicle, disintegrator, lubricant, binder, dispersant, plasticizer or diluent.

24. A method of preventing the physiological role of endothelial action by administering an effective amount of a compound according to claim 1 or a pharmacologically acceptable salt thereof to a mammal in need thereof.

25. A method of preventing the production of IL-1 by administering an effective amount of a compound according to claim 1 or a pharmacologically acceptable salt thereof to a mammal in need thereof.

26. A method of stimulating the production of NGF by administering an effective amount of a compound according to claim 1 or a pharmacologically acceptable salt thereof to a mammal in need thereof.

* * * * *